(12) United States Patent
Ptaszek et al.

(10) Patent No.: US 12,387,852 B2
(45) Date of Patent: Aug. 12, 2025

(54) APPARATUS AND METHOD FOR GENERATING CLINICAL DECISION SUPPORT

(71) Applicant: Anumana, Inc., Cambridge, MA (US)

(72) Inventors: Leon Ptaszek, Milton, MA (US); Rohit Jain, Danville, CA (US); Anand Ramani, Fresno, CA (US); Animesh Agarwal, San Mateo, CA (US); Yogisha Heggadahalli Jayendra, Bengaluru (IN); Sanjeev Shrinivas Nadapurohit, Bengaluru (IN); Karthik K. Bharadwaj, Bengaluru (IN); Shashi Kant, Bengaluru (IN); Shiva Verma, Bangalore (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/785,860

(22) Filed: Jul. 26, 2024

(65) Prior Publication Data
US 2025/0210206 A1    Jun. 26, 2025

Related U.S. Application Data

(60) Provisional application No. 63/614,858, filed on Dec. 26, 2023.

(51) Int. Cl.
  *G16H 20/40* (2018.01)
  *G16H 50/30* (2018.01)
  *G16H 70/20* (2018.01)

(52) U.S. Cl.
  CPC ............. *G16H 70/20* (2018.01); *G16H 20/40* (2018.01); *G16H 50/30* (2018.01)

(58) Field of Classification Search
  None
  See application file for complete search history.

(56) References Cited

U.S. PATENT DOCUMENTS

| | | | |
|---|---|---|---|
| 2008/0154132 A1* | 6/2008 | Hall | A61N 7/02 600/439 |
| 2013/0282005 A1* | 10/2013 | Koch | A61B 90/36 606/41 |

(Continued)

FOREIGN PATENT DOCUMENTS

| | | |
|---|---|---|
| CN | 116646013 A | 8/2023 |
| CN | 116646078 A | 8/2023 |

(Continued)

OTHER PUBLICATIONS

S. Bozyel et al; Artificial Intelligence-Based Clinical Decision Support Systems in Cardiovascular Diseases; "The Anatolian Journal Of CardiologyAvailable Online Date: Jan. 1, 2024".

(Continued)

*Primary Examiner* — John A Pauls
(74) *Attorney, Agent, or Firm* — Caldwell Intellectual Property Law

(57) ABSTRACT

An apparatus and method for generating clinical decision support is disclosed. The apparatus includes at least a processor and a computer-readable storage medium communicatively connected to the at least a processor, wherein the computer-readable storage medium contains instructions configuring the at least processor to receive user data, generate a fused feature vector correlating the user data to a plurality of clinical outcomes by training a plurality of deep neural networks (DNNs) to output a first set of feature vectors, a second set of feature vectors and a third set of feature vectors, fusing the first, second, and third set of features vectors to form the fused feature vector, generate a procedural output using the fused feature vector, and display the procedural output through a user interface.

20 Claims, 12 Drawing Sheets

(56) References Cited

U.S. PATENT DOCUMENTS

2014/0022250 A1* 1/2014 Mansi ............... G06T 7/149
                 345/420
2015/0366500 A1* 12/2015 Aoyagi ............ G06T 7/0012
                 600/407

FOREIGN PATENT DOCUMENTS

| WO | WO-2022060948 A1 * | 3/2022 | ......... A61B 5/02055 |
| WO | 2022079623 A1 | 4/2022 | |

OTHER PUBLICATIONS

S. Tang et al; Machine Learning-Enabled Multimodal Fusion of Intra-Atrial and Body Surface Signals in Prediction of Atrial Fibrillation Ablation Outcomes; Circ Arrhythm Electrophysiol. Aug. 2022; 15(8).

* cited by examiner

APPARATUS AND METHOD FOR GENERATING CLINICAL DECISION SUPPORT

CROSS-REFERENCE TO RELATED APPLICATIONS

This application claims the benefit of priority of U.S. Provisional Patent Application Ser. No. 63/614,858, filed on Dec. 26, 2023, and titled "SYSTEM AND METHOD FOR CLINICAL DECISION SUPPORT," which is incorporated by reference herein in its entirety.

FIELD OF THE INVENTION

The present invention generally relates to the field of treatment plan generation for clinical decision support. In particular, the present invention is directed to an apparatus and method for generating clinical decision support.

BACKGROUND

Arrhythmias are cardiac rhythm disorders that pose a significant challenge in clinical settings. Traditional approaches to the diagnosis and treatment of arrhythmia involve standardized protocols that may not fully account for the unique characteristics of individual patients. Current methods often rely on manual interpretation of cardiac-related signals and limited data integration, leading to sub-optimal treatment outcomes. There is a recognized need for an innovative software solution that harnesses advanced data analytics, artificial intelligence, and machine learning techniques to enable healthcare professionals to make informed and personalized clinical decisions for patients for the treatment of atrial fibrillation.

SUMMARY OF THE DISCLOSURE

In an aspect, an apparatus for generating clinical decision support is disclosed. The apparatus includes at least a processor and a computer-readable storage medium communicatively connected to the at least a processor, wherein the computer-readable storage medium contains instructions configuring the at least processor to receive user data, generate a fused feature vector correlating the user data to a plurality of clinical outcomes by training a plurality of deep neural networks (DNNs) to output a first set of feature vectors, a second set of feature vectors and a third set of feature vectors, fusing the first, second, and third set of features vectors to form the fused feature vector, generate a procedural output using the fused feature vector, and display the procedural output through a user interface.

In another aspect a method for generating clinical decision support is disclosed. The method includes receiving, by a computing device, user data, generating, by the computing device, a fused feature vector correlating the user data to a plurality of clinical outcomes by training a plurality of deep neural networks (DNNs) to output a first set of feature vectors, a second set of feature vectors and a third set of feature vectors, fusing the first, second, and third set of features vectors to form the fused feature vector, generating, by the computing device, a procedural output using the fused feature vector, and displaying, by the computing device, the procedural output through a user interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
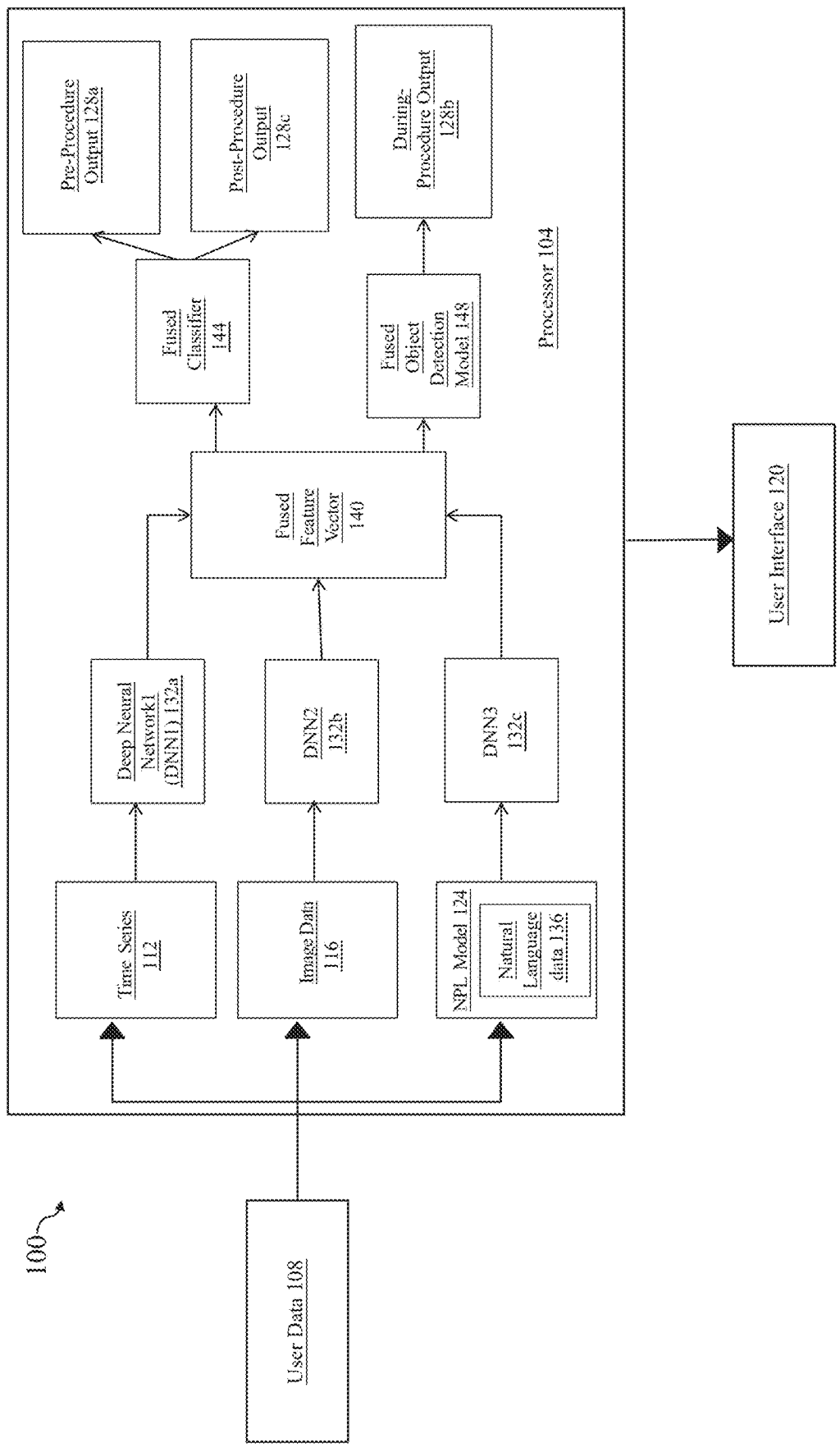
FIG. 1 is an exemplary embodiment of an apparatus for generating clinical decision support.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Atrial fibrillation (AF) is the most common arrhythmia in adults and affects a large number of the adult population. The incidence and prevalence of AF are increasing in association with aging of the population. Either medications or ablation procedures can be utilized to minimize the burden of AF. Utilization of ablation procedures are growing, as it is more effective than medical therapy. Although ablation is more effective than pharmacotherapy, limitations in ablation technology result in frequent recurrences of AF after treatment. These recurrence rates persist despite recent advances in ablation technology, including refinement of the electroanatomic mapping systems and catheters utilized in ablation procedures. Recurrence of AF after ablation procedures is associated with significant patient morbidity and utilization of health care resources. Improvement in the effectiveness of ablation procedures for atrial fibrillation as well as pre- and post-ablation medical management of atrial fibrillation could produce better patient outcomes and reduce health care costs.

Effective treatment of atrial fibrillation requires that clinicians make multiple integrative assessments of a patient. Given the large volume of data and multiple types of relevant data (ECG, EGM, imaging, patient historical data), clinicians may struggle with timely procurement and processing of large volumes of data for prompt decision and treatment strategy. Furthermore, treatment of atrial fibrillation with ablation is particularly complex and requires that clinicians make integrative assessments of multiple types of data simultaneously. It is possible that failure of clinicians to detect subtle changes in multiple streams of data contribute to suboptimal effectiveness of atrial fibrillation treatment with the current state of the art. Currently, there are no available clinical decision support tools to assist clinicians in organizing and prioritizing the data that must be analyzed. A clinical decision support tool that collects multiple types of data and draws the clinician's attention to the most relevant findings could improve procedure efficacy and safety.

At a high level, aspects of the present disclosure are directed to apparatuses and methods for generating clinical decision support. An embodiment of the present disclosure provides a machine learning-based system for clinical decision support that integrates multiple types of patient data (e.g., surface electrocardiograms (ECGs), intracardiac electrocardiograms (EGMs), cardiac imaging studies (echocardiograms, cardiac CT, cardiac MRI), non-cardiac imaging, and patient historical data). The system is configured to assist clinicians in the management of atrial fibrillation at multiple points in a patient's care journey, including, for example, planning for an ablation procedure, performing an ablation procedure, and management of patients after an ablation procedure.

In other embodiments, the apparatuses and methods disclosed herein may be configured to assist clinicians in the management and treatment of a plurality of cardiac conditions, morbidities, symptoms, and the like. For example, heart conditions may include various types of arrhythmias or arrhythmia-related conditions/symptoms such as Supraventricular Tachycardia (SVT), Atrial Flutter, Wolff-Parkinson-White Syndrome (WPW), Ventricular Tachycardia (VT), abnormal pathways connecting different parts of the heart causing arrhythmias, Bundle Branch Re-entrant Tachycardia, Atrial Tachycardia, arrhythmias in structural heart disease, and the like. Furthermore, heart conditions, morbidities, symptoms, and the like may be non-arrhythmia-related, such as Hypertrophic Cardiomyopathy (HCM), heart failure, Symptomatic Premature Ventricular Contractions (PVCs), Atrial Flutter without overt arrhythmia symptoms, congenital heart defects, Pulmonary Vein Stenosis, and the like. Additionally, the apparatuses and methods disclosed herein may be used to assist clinicians in the preventive care of cardiac issues. For example, the apparatuses and methods disclosed herein may be used as a preventive measure to mitigate the risk of stroke and heart failure in patients with asymptomatic or minimally symptomatic atrial fibrillation (AFib). Another preventive application of cardiac ablation may be in patients with conditions like Hypertrophic Cardiomyopathy (HCM) or frequent premature ventricular contractions (PVCs). In HCM, ablation can be used to strategically reduce the thickness of the heart muscle, preventing future obstruction of blood flow and reducing the risk of sudden cardiac death. Similarly, in patients with frequent PVCs, even in the absence of overt cardiomyopathy, ablation can prevent the progression to heart failure and alleviate subtle symptoms that might impact quality of life over time. The apparatuses and methods disclosed herein may be used as a preventive measure to address underlying electrical disturbances in the heart before they lead to severe clinical outcomes.

Some embodiments of the present disclosure will now be described more fully hereinafter with reference to the accompanying drawings, in which some, but not all, embodiments of the disclosure are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout. Also, reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Further, the terms "a" and "an" herein do not denote a limitation of quantity, but rather denote the presence of at least one of the referenced item. Moreover, various features are described which may be exhibited by some embodiments and not by others. Similarly, various requirements are described which may be requirements for some embodiments but not for other embodiments.

The embodiments are described herein for illustrative purposes and are subject to many variations. It is understood that various omissions and substitutions of equivalents are contemplated as circumstances may suggest or render expedient but are intended to cover the application or implementation without departing from the spirit or the scope of the present disclosure. Further, it is to be understood that the phraseology and terminology employed herein are for the purpose of the description and should not be regarded as limiting. Any heading utilized within this description is for convenience only and has no legal or limiting effect.

Exemplary embodiments illustrating aspects of the present disclosure are described below in the context of several specific examples.

Referring now to FIG. 1, an exemplary embodiment of an apparatus 100 for generating clinical decision support is illustrated. Apparatus 100 include a processor 104. A computing device includes a processor communicatively connected to a memory. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software and the like) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, apparatus 100 may be deployed in before ablation procedure stage or before ablation procedure point of patient's care. At this point, apparatus 100 may provide an operator of apparatus 100 with input or clinical decision support regarding the regions of a patient's heart that should be ablated as well as provide focused information regarding procedural safety. Apparatus 100 may be deployed in during ablation procedure stage or during ablation procedure point of patient's care. At this point, apparatus 100 may provide the operator of apparatus 100 with input or clinical decision support regarding confirmation for a success for each of individual ablation lesions, as well as provide the operator with an estimated likelihood of an overall success for the ablation procedure. In this stage, apparatus 100 may integrate multiple types of data including, but not limited to, dynamic changes in surface ECG and intracardiac electrograms associated with ablation, as well as dynamic changes in other ablation metrics, patient history, locations of the heart ablated, and success of the ablations performed in the context of data from patients who have undergone comparable procedures in the past. Further, apparatus 100 may be deployed in after ablation procedure stage or after ablation procedure point of patient's care. At this point, apparatus 100 may provide the operator of apparatus 100 with input or clinical decision support regarding medical therapy (e.g., anticoagulation) and frequency of ambulatory arrhythmia assessments based on integrated multiple types of data. This may ensure that the operator and/or the clinicians are monitoring and assessing performance of the heart of the patient regularly. This may also reduce chances of recurrence of AF.

Still referring to FIG. 1, processor 104 is configured to receive user data 108. "User data," as used herein, is data related to a user. A user may be person, such a patient of a medical provider or institution. User data 108 as described herein may be received or indexed by processor in a time series 112, such as at various time intervals before, during, and after an ablation procedure. User data 108 may include multiple types of data such as a surface electrocardiogram (ECG), intracardiac electrocardiogram (EGM), cardiac and non-cardiac imaging, and user historical data. The diversity in user data 108 may provide a significant improvement over conventional techniques for clinical decision making that only analyzes individual type of data relating to patient. A "surface electrocardiogram (ECG)", as used herein is a record of electrical activity of the heart. The ECG provides information about the heart's rate and rhythm, and can indicate the presence of heart enlargement, heart attacks, or arrhythmias. ECG data/information may include digital ECG data and/or analog ECG data. As used in the current disclosure, "digital ECG data" refers to the digital representation of the electrical activity of the heart recorded over time. As used in the current disclosure, "analog ECG data" refers to an analog representation of the electrical activity of the heart recorded over time. ECG data may include a plurality of ECG signals represented in a digital or analog format. As used in the current disclosure, a "format" refers to a method of representing information or data using continuous and continuously variable physical quantities, such as electrical voltage. Electrical activity may be depicted using electrocardiogram (ECG) signals. As used in the current disclosure, a "electrocardiogram signal" is a signal representative of electrical activity of heart.

The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG signal can help diagnose various heart conditions, such as arrhythmias, myocardial infarction (heart attack), conduction abnormalities, and electrolyte imbalances Still referring to FIG. 1, ECG data may include a 12-lead ECG. A "12-lead ECG," as used herein, is a recording of the electrical activity of the heart from multiple angles. An "intracardiac electrocardiogram (EGM)," as used herein, is a recording of electrical activity of the heart, measured by monitoring changes in electric potential. EGMs provide detailed information about the heart's electrical activity, particularly useful for pinpointing areas that generate abnormal electrical signals. User data 108 may include image data 116 such as cardiac images and non-cardiac images. "Cardiac images," as used herein, are visual representation of the heart. Cardiac images may show the structure, function, and blood flow of the heart and may be used for detecting and managing diseases such as coronary artery disease, heart failure, and valve disorders. Examples of cardiac images include echocardiograms, cardiac magnetic resonance (MRI) images, cardiac computed tomography (CT) images, nuclear cardiac imaging (PET and SPECT) images, cardiac ultrasound (Echocardiography data) and the like. Non-cardiac images, while not directly visualizing the heart, my provide essential information relevant to cardiac health. For example, chest x-rays may include a picture of the chest, including the lungs, ribs, and heart shadow. It may reveal signs of heart failure, such as an enlarged heart or fluid in the lungs (pulmonary edema) and may also show calcifications in the aorta or other large vessels that may suggest underlying vascular disease. Other examples of non-cardiac images include abdominal ultrasound, carotid ultrasound, pulmonary imaging (such as CT scans of the lungs), brain imaging, and the like. "User historical data," as used herein, is information related to a user's past medical information. User historical data may include detailed records of past diagnoses, treatments, and outcomes. This includes major illnesses, chronic conditions, hospitalizations, surgeries, and any complications or outcomes from those treatments. User historical data may include a list of all medications a patient has taken or is currently taking, including prescription drugs, over-the-counter medications, and supplements. User historical data may include information about health disorders that occur in a patient's family, which can provide insights into genetic or hereditary conditions that might affect the patient. Conditions like heart disease, diabetes, and cancer in close relatives can indicate an increased risk for these disorders. User historical data may include data on lifestyle factors that can impact health, including smoking, alcohol use, exercise, dietary habits, and occupational hazards. User historical data may include records of any allergies to medications, foods, or environmental factors. User historical data may include documentation of any symptoms the patient has experienced, which can help in diagnosing new conditions or monitoring the progression of existing ones.

Still referring to FIG. 1, user historical data may include an electronic health record. An "electronic health record (EHR)," as used herein, is an electronic version of a user's medical history. An EHR may be maintained by a provider, such as a physician, over time, and may include all of the key administrative clinical data relevant the user's care under a particular provider, including demographics, progress notes, problems, medications, vital signs, past medical history, immunizations, laboratory data and radiology reports. For example, EHR demographics may include age, gender, socioeconomic status, geographic location, marital status, language/communication needs and the like.

Still referring to FIG. 1, user historical data or user data 108 in general may indicate a history of Paroxysmal or Persistent Atrial Fibrillation (AF) of the user. Paroxysmal AF refers to a type of atrial fibrillation characterized by sudden, unpredictable episodes of arrhythmia that start and stop abruptly, typically lasting less than 7 days and often resolving within 24 hours. Persistent AF refers to an atrial fibrillation episode that lasts longer than 7 days. Unlike paroxysmal AF, these episodes do not stop on their own and require medical intervention such as medication or electrical cardioversion to restore normal rhythm.

Still referring to FIG. 1, user historical data or user data 108 in general may indicate a history of typical or atypical atrial flutters. A typical atrial flutter is a condition involving a rapid but regular heart rhythm originating in the right atrium. It is often caused by a reentrant circuit moving around the tricuspid valve in a counterclockwise or clockwise direction. An atypical atrial flutter is less structured than typical flutter and can originate from either the right or left atrium. It usually occurs in individuals who have had previous heart surgery or ablation, and its circuit patterns are more varied and complex.

Still referring to FIG. 1, user historical data or user data 108 in general may indicate a history of prior ablation or comorbidities. A history of prior cardiac ablation procedures is relevant because it can influence the current strategy for managing arrhythmias. Ablation scars themselves can alter the heart's electrical pathways and potentially serve as new foci or barriers for arrhythmic circuits, impacting both the likelihood of recurrence and the approach to further treatment. Comorbidities are other coexisting medical conditions that the patient has alongside their primary diagnosis of atrial fibrillation or flutter. Common comorbidities in AF patients include hypertension, heart failure, diabetes, and thyroid disorders. The presence of these conditions can affect the choice of treatment strategies and medications, impact the prognosis, and influence the management of AF or flutter, including decisions regarding anticoagulation and the use of certain antiarrhythmic drugs.

Still referring to FIG. 1, user data 108 may include catheter data in relation to an ablation procedure. Catheter data may include all the information and measurements gathered from the catheter prior or during the procedure. Catheter data may include recordings of electrical signals from the heart, which help identify the abnormal pathways or regions responsible for the arrhythmia. Electrical signals are important for mapping the heart's electrical activity and targeting the correct areas for ablation. Cather data may include positional data which refers to the location and orientation of the catheter within the heart. Positional data may further include a catheter positional stability. For an ablation procedure to be successful, the catheter must remain stable at the targeted location within the heart. This stability ensures that the energy delivered is precise and consistent, minimizing the risk to surrounding tissues and increasing the efficacy of the ablation. Catheter data may include temperature data including information regarding the heat being applied to cardia tissues. Temperature data may track how cold the catheter tip becomes. This temperature monitoring helps control the ablation process to prevent over- or under-treatment of tissue. Catheter data may include a catheter contact force recording the to which the catheter tip contacts the heart tissue affects the quality and size of the lesion.

Still referring to FIG. 1, user data 108 may include ablation delivery data. "Ablation delivery data," as used herein, is the parameters and settings used during an ablation procedure to apply therapeutic energy to heart tissue. Ablation delivery data may dictate the efficacy, safety, and outcome of the procedure. Ablation delivery data may include cryoablation data. "Cryoablation," as used herein, is a medical procedure used to treat cardiac arrhythmias, such as atrial fibrillation, as well as other conditions in different parts of the body. It involves the use of extreme cold to destroy abnormal tissues that contribute to irregular heart rhythms. Cryoablation data may include the minimum temperature and duration of the of the procedure. Ablation delivery data may include radiofrequency (RF) ablation data. "Radiofrequency ablation," as used herein, is a medical procedure used to treat various types of cardiac arrhythmias, including atrial fibrillation, atrial flutter, and ventricular tachycardia. It involves the use of radiofrequency energy to heat and destroy small areas of heart tissue that are causing abnormal electrical signals. RF data may include the power, the amount of electrical energy delivered to the tissue, measured in watts, and duration of the procedure. Ablation data may include pulsed field ablation (PFA) data. "Pulsed Field Ablation," as used herein, is a procedure that uses short bursts of high-intensity electrical fields to create lesions and disable unwanted electrical pathways in the heart. PFA data may include the duration of the procedure.

Still referring to FIG. 1, processor 104 may receive user data 108 as input through a user interface 120. A "user interface," as used herein, is a means by which a user and a computer system interact; for example, through the use of input devices and software. A user interface 120 may include a graphical user interface (GUI), command line interface (CLI), menu-driven user interface, touch user interface, voice user interface (VUI), form-based user interface 120, any combination thereof, and the like. A user interface 120 may include a smartphone, smart tablet, desktop, or laptop operated by the user. In an embodiment, the user interface 120 may include a graphical user interface 120. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs and the like because clicking on them yields instant access. Information contained in user interface 120 may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like. Additionally or alternatively the user interface 120 may integrate a chatbot to receive user data 108. For example, the chatbot may greet a patient and ask for data related to filling out a user profile such as basic identification details like name and date of birth.

Still referring to FIG. 1, processor 104 may receive user data 108 from a user database. A "user database," as used herein, is data structure contacting data related to a user. Databases as described herein may be implemented, without limitation, as a relational database, a key-value retrieval database such as a NOSQL database, or any other format or structure for use as a database that a person skilled in the art would recognize as suitable upon review of the entirety of this disclosure. Databases may alternatively or additionally be implemented using a distributed data storage protocol and/or data structure, such as a distributed hash table or the like. Databases may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. In some embodiments, the user database may be populated by the chatbot, or from inputs received through the user interface 120.

Still referring to FIG. 1, processor 104 may be configured to classify the user data 108 into a procedure category. A "procedure category," as used herein, is data containing information before, during or after an ablation procedure. Procedure categories may include a pre-procedure category, a during-procedure category and a post-procedure category.

Still referring to FIG. 1, classifying user data 108 to a procedure category may include implementing a natural language processing (NPL) model 124. An NPL model 124 may be generated using a language processing module. A language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may operate to produce a language processing model 124. Language processing model 124 may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to 1, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Alternatively or additionally, and with continued reference to FIG. 1, language processing module may be produced using one or more large language models (LLMs). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of an LLM may include information from one or more public or private databases. As a non-limiting example, training sets may include databases associated with an entity. In some embodiments, training sets may include portions of documents associated with the electronic records 112 correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

Continuing to refer to FIG. 1, generating language processing model 124 may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module may use a corpus of documents to generate associations between language elements in a language processing module, and diagnostic engine may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York Still referring to FIG. 1, processor 104 may train the NPL model 124 with a pre-procedure text dataset, a during-procedure text dataset, and a post-procedure text dataset. A "pre-procedure text dataset," as sued herein, is data correlating user data. In some cases, pre-procedure text dataset may include documents and notes related to patient preparation, consent forms, pre-operative assessments, and scheduling information to a pre-pedicure category criteria. For example user data 108 labeled or indicating pre-operative lab work, such as a user's complete blood test, may be classified to a pre-procedure category. A "during-procedure text dataset," as used herein, is data correlating user data, such catheter data and ablation delivery data, to a during-procedure category criteria. A during-procedure text dataset may include data correlating user data 108, such as ECG data and user historical data, to a post-procedure category criteria. A "post-procedure text dataset," as used herein, is data correlating user data, such as recovery notes, follow-up appointments, patient feedback, and outcome measurements, to a post-procedure category criterion. A post-procedure text dataset may include documents and notes that detail patient status and medical follow-ups after a procedure is completed, such as discharge summaries, pain assessment records, and complication reports. These data points can be leveraged to analyze the efficacy of the procedure, predict recovery outcomes, and enhance patient care for future cases. Processor 104 may first pre-process user data 108 by cleaning, tokenizing, and additionally using techniques like TF-IDF or embeddings for feature extraction. The NPL model 124 may include supervised learning model such as a Support Vector Machine (SVM), a neural network, or a transformer-based model like BERT to understand context of user data 108.

Still referring to FIG. 1, processor 104 may classify user data 108 to a procedure category using an image classifier. Similar to the NPL model, the image classifier may be trained on datasets correlating images of user data 108 to procedure category images. For example, training data may include echocardiograms showing the heart before the ablation categorized to a pre-procedure category. The image classifier may include a convolutional neural network (CNN) architecture such as LeNet for less complex images or more advanced architectures like AlexNet, VGG, or ResNet for more detailed and high-dimensional images. During training, the CNN may learn to recognize patterns and features in the images that are indicative of their procedural categories through the adjustment of internal weights based on a loss function, which measures the difference between the predicted and actual labels. In an CNN training embodiment, during a forward pass, an image may be passed through the CNN wherein the output may be predictions indicating the probabilities of the image belonging to each of the procedural categories (e.g., pre-procedure, during-procedure, post-procedure). The difference between the predicted probabilities and the actual label of the image may be calculated using a loss function, such as a cross-entropy loss function. This function may calculate the total loss based on how far the CNN model's predictions are from the actual class. Once the loss is calculated, backpropagation may be used to calculate the gradient of the loss function with respect to each weight in the network. This process may include applying a chain rule to find these gradients step-by-step from and output layer of the CNN back to the first hidden layer of the CNN. The weights may then be updated using an optimization algorithm like Stochastic Gradient Descent (SGD) or Adam. This process may include adjusting the weights in a direction that minimizes the loss. The size of the step that the weights are adjusted may be controlled by a parameter referred to as a learning rate. The learning rate is a hyperparameter that controls how much the weights in the network are adjusted with respect to the gradient of the loss function during training. Classification of user data 108 to a procedural category may be used to derive inputs into machine learning models as described further below.

Still referring to FIG. 1, processor 104 is configured to generate a procedural output 128 based on the procedure category. A "procedural output," as used herein, is a set of data and insights generated before, during, and after a medical procedure, such as cardiac ablation. A procedural output 128 may include a pre-procedure output 128a. A "pre-procedure output," as used herein, is data generated regarding information applicable prior to the performance of a procedure. Pre-procedure output 128a may include, but is not limited to, an ablation strategy (for example, based on a pulmonary vein potential (PVP) or pulmonary vein isolation (PVI), and/or posterior wall isolation (PWI)). The pre-procedure output 128a may provide clinical decision support to an operator with input regarding regions of the patient's heart that should be ablated as well as provide focused information regarding procedural safety. Further, the pre-procedure output 128a may indicate the ablation treatment plan (e.g., structures to be targeted during the ablation procedure). The pre-procedure output 128a may be provided to a user interface 120 as described above. An "ablation strategy," a used herein, is a data structure outlining focuses on key aspects of cardiac ablation, particularly for conditions like atrial fibrillation, where abnormal electrical pathways in the heart need to be interrupted to restore normal rhythm. The ablation strategy may be based on elements such as pulmonary vein potential (PVP), pulmonary vein isolation (PVI), and posterior wall isolation (PWI). Pulmonary vein potentials are electrical signals that originate from or around the pulmonary veins. These veins are common sources of ectopic beats that initiate atrial fibrillation. Recognizing the patterns of PVP is crucial for identifying the specific areas around the pulmonary veins that might be contributing to arrhythmia. The ablation strategy may include detailed maps showing the electrical activity around the pulmonary veins or other visualizations highlighting areas of interest or concern, such as regions of rapid electrical firing or irregular potentials. This information guides the precise targeting during ablation to interrupt these ectopic foci.

Still referring to FIG. 1, generating detailed maps showing the electrical activity around the pulmonary veins or other visualizations highlighting areas of interest or concern may include an integration of imaging and mapping technologies. Processor 104 may receive detailed electrical and anatomical data from user data 108 regarding electrophysiological mapping (electrophysiological mapping may have been performed on a patient using specialized catheters equipped with multiple electrodes that measure the electrical activity directly from within the heart, particularly around the pulmonary veins). Simultaneously, imaging techniques like intracardiac echocardiography (ICE), computed tomography (CT), or magnetic resonance imaging (MRI) provide high-resolution images of the heart's structure. Processor 104 my integrate these diverse data sets into a coherent visualization. Software platforms such as CARTO (by Biosense Webster) and EnSite (by Abbott) may be implemented to overlay the real-time electrical data collected from the catheters onto the anatomical images obtained from the imaging studies. This integration allows for a precise anatomical correlation with electrical activity, enabling clinicians to see exactly where abnormal electrical signals are originating relative to the heart's anatomy. Processor 104 may then use algorithms to process this integrated data to create detailed electro anatomical maps. These algorithms may include image segmentation techniques that differentiate cardiac tissues based on their characteristics in the images, or pattern recognition algorithms that identify and highlight areas of abnormal electrical activity. For example, algorithms within the CARTO system can detect and visually enhance regions showing rapid electrical firing or irregular potentials, making them easily identifiable on the map.

Still referring to FIG. 1, PVI aims to electrically isolate the pulmonary veins from the left atrium. This is done to prevent the pulmonary vein potentials from triggering atrial fibrillation. The ablation involves creating a series of lesions (scar tissue) around the entrances of the pulmonary veins to block any abnormal electrical signals. This is typically achieved using techniques like radiofrequency ablation or cryoablation. The ablation strategy may include detailed plans outlining the target areas for ablation around the pulmonary veins, including depth and intensity of ablation needed. The ablation strategy may include step-by-step guides or checklists that assist in preparing the ablation procedure, presented in a sequential and easy-to-follow manner. The ablation strategy may include an analysis of potential risks associated with PVI, such as damage to nearby structures. The ablation strategy may include risk maps and graphical representations of the heart showing high-risk areas and proposed safe ablation zones.

Still referring to FIG. 1, the posterior wall of the left atrium is another site where atrial fibrillation can be maintained. Isolating this wall can be crucial for patients who continue to experience arrhythmias despite pulmonary vein isolation. Similar to PVI, PWI involves creating a pattern of lesions on the posterior wall of the left atrium to disrupt the pathway of the arrhythmia. This is more complex due to the proximity to other critical structures. The ablation strategy may include imaging and functional data that provide insights into the thickness and electrical properties of the posterior wall of the left atrium.

Still referring to FIG. 1, the ablation strategy may include 3D models of the atrium that can be manipulated to view from different angles, highlighting areas that require isolation. The ablation strategy may include customized ablation paths tailored to a patients anatomy and electrical mapping data. Generating 3D models of the heart for clinical decision support in cardiac ablation may include a multi-step process that begins with data acquisition. This first step may use advanced imaging modalities such as Computed Tomography (CT), which offers high-resolution cross-sectional images, and Magnetic Resonance Imaging (MRI), known for detailed soft tissue contrast that is crucial for visualizing heart structure and function. Other techniques, like 3D echocardiography, can also provide valuable real-time images of the heart's internal structures and dynamics. Each of these technologies may be used independently by the process or in combination to gather comprehensive anatomical and functional data from user data 108. After collecting the necessary images, the next phase is data processing and model construction. Here, specialized software may be employed to convert the 2D images from various angles into a coherent 3D model. This process may involve segmentation, where the heart's boundaries are identified and differentiated from other thoracic structures. Advanced algorithms then stitch these segmented images together to form a detailed 3D representation of the heart. These algorithms may vary from simple thresholding methods that separate pixels based on intensity to more complex machine learning models like Convolutional Neural Networks (CNNs), which the processor 104 can train learn to identify the heart's contours from vast datasets of annotated images. Once segmentation is complete, the outlined regions may be used to build the 3D model through a process known as volume rendering or surface reconstruction. For example, the marching cubes algorithm is a technique used for surface reconstruction; it converts the segmented image data into a 3D surface mesh by tracing the edges of segmented areas across sequential slices. This mesh accurately represents the shape and size of the heart and can be further refined to include textures and colors that enhance visual understanding.

Still referring got FIG. 1, the ablation strategy may include strategies to mitigate identified risks, such as suggesting changes in the catheter's path or the use of lower energy settings in areas close to sensitive structures. Generating such strategies may include processor 104 preforming a comprehensive assessment of potential risks using user data 108 received from advanced imaging technologies like cardiac MRI, CT scans, and intracardiac echocardiography (ICE). These modalities provide high-resolution images of the heart and surrounding structures, helping to identify areas where critical tissues or vessels may be at risk during ablation. Based on this detailed mapping and imaging data, specific strategies, processor 104 may generate recommendations for risk mitigation using methods such as spatial analysis, risk modeling, and the like. For example, to determine the proximity of the ablation target areas to sensitive structures a spatial analysis may be performed to calculate distances and potential overlap between the planned ablation sites and these critical areas. In another example, using historical data and predictive modeling, processor 104 may use a risk model to assess the likelihood of adverse effects based on the proximity of the ablation site to sensitive structures. This risk model factors in patient-specific variables and procedural details to tailor the risk assessment. Utilizing machine learning techniques, the risk model analyzes patterns from historical procedural data and patient outcomes to predict risks. This may include learning from past cases where similar proximity to sensitive structures resulted in complications, thereby refining the risk estimates for current procedures. The risk model may generate a risk score for each potential ablation site, which quantifies the likelihood of adverse effects based on proximity to sensitive structures and the predictive modeling outcomes. Based on the risk scores, the risk model may output recommendations. For instance, if a particular ablation site is too close to the phrenic nerve, the risk model might suggest either relocating the ablation site or reducing the energy delivered to minimize nerve damage. As the procedure progresses, the risk model continuously updates risk assessments based on real-time data, allowing for dynamic adjustments to the ablation strategy. This ensures that the procedure remains as safe as possible by adapting to the evolving procedural landscape.

Still referring to FIG. 1, pre-procedure output 128a may include alerts to the operator to potential risks, such as proximity to critical structures like the esophagus, phrenic nerve, or coronary arteries, which could be damaged during the procedure. optimal settings for the ablation device (e.g., power settings for RF ablation, duration, and size of lesions) based on the target tissue's characteristics and location. Pre-procedure output 128a may include optimal settings for the ablation device (e.g., power settings for RF ablation, duration, and size of lesions) based on the target tissue's characteristics and location. Pre-procedure output 128a may include recommendations on regions of the heart that should be targeted for ablation. For example, areas around the pulmonary veins may be suggested for isolation in cases of atrial fibrillation. Pre-procedure output 128a may include Still referring to FIG. 1, a "during-procedure output," as used herein, is data generated regarding information applicable during the performance of a procedure The during-procedure output 128b may be further divided into three stages, i.e., pre-procedure (such as right before the ablation procedure), intraprocedural visualization (such as, visualization of the ongoing ablation procedure for each ablation lesion) and intraprocedural evaluation of ablation (such as, evaluation of a currently performed ablation of a lesion while the ablation procedure is ongoing). For example, the during-procedure output 128b in the pre-procedure stage may include ablation strategy data, for example, to perform ablation on pulmonary veins or posterior wall, and targeting of atrial flutter. The during-procedure output 128b in the intraprocedural visualization stage may include, for example, visualization data of intracardiac EGMs before ablating, assessment data of intracardiac EGMs during ablation, and assessment data of intracardiac EGMs after ablation. The during-procedure output 128b in the intraprocedural evaluation stage may include, for example, integrative assessment data to assess lesion quality and contiguity, and post-ablation summative assessment data of durability of ablation that would give operator an estimate of likelihood of AF recurrence based on chosen ablation strategy and quality of lesion delivery. It may be noted, the post-ablation summative assessment data may not just provide a total difference in ablation metrics before/after ablation but also a rate of change after the ablation procedure. The during-procedure output 128b may be provided in a user interface 120 relating to a mapping system, a recording system interface, or a dedicated user interface 120 with possible population of data in EHR system.

Still referring to FIG. 1, in generating the intraprocedural evaluation of ablation, processor 104 may implement algorithms and machine learning models to analyze the EGM data along with the imaging data to evaluate the quality of a lesion. These models can predict the effectiveness of the ablation based on the characteristics of the lesion, such as size, depth, and transmurality. Processor 104 may generate integrative assessment data by combining inputs from various during-procedure data points, such as catheter position, amount of energy delivered, duration of energy application, and real-time EGM changes. Algorithms analyze this data to provide feedback on the contiguity and completeness of the ablation lines. A machine learning model may then be used to estimate the durability of the lesions. The machine learning model may be configured to analyze trends in the EGM characteristics pre- and post-ablation and correlate these with historical data on long-term outcomes to predict the likelihood of arrhythmia recurrence. Post-ablation summative assessment data may be generated using a machine learning model to assess the overall quality of the ablation based on comprehensive during-procedure data. The machine learning model may be configured to analyze factors such as the rate of change in EGM signals post-ablation, lesion quality, and procedural metrics to estimate the likelihood of arrhythmia recurrence. calculate the rate of change in ablation metrics, providing insights into the immediate effects of the ablation and predicting long-term success or potential complication.

Still referring to FIG. 1, in an example, during the ablation process, apparatus 100 may configured to provide clinical decision support by utilizing patient-specific information to assist the clinician to correctly identify intracardiac electrograms in the areas of the heart targeted for ablation. Processor 104 may implement artificial intelligence/machine learning processes to analyze the EGM signals in user data 108 to identify patterns typical of arrhythmic sites. This may include identifying rapid, irregular, or fractionated electrical signals that suggest pathological areas. For example a machine learning model may be trained to differentiate between normal and pathological electrical signals such as those representing scar tissues or ectopic foci, based on characteristics like signal amplitude, frequency, and irregularity. Deep learning models, particularly convolutional neural networks (CNNs) and recurrent neural networks (RNNs), may be used to analyze sequences of EGM signals to detect subtle patterns that might be missed by traditional methods. These models can provide a continuous assessment of signal characteristics during the procedure, offering insights into the dynamic changes occurring as ablation impacts the tissue. Processor 104 may then visualize the recognize patterns on a user interface 120, overlaying electrogram data onto the anatomical images of the heart. AI algorithms may enhance the visualization of EGM data by integrating it with real-time imaging data from ICE, CT, or MRI. Techniques like image segmentation and registration can be applied to align and overlay the electrogram data precisely onto the 3D images of the heart's anatomy. This provides a more intuitive visual representation of where electrical abnormalities are located relative to the heart's structure. Furthermore, based on the analysis by the machine learning model, processor 104 may generate actionable insights and recommendations. For example, if an area with abnormal electrograms corresponds to a site previously identified via imaging as potentially arrhythmogenic, processor 104 may validate this site as a target for ablation.

Still referring to FIG. 1, the during-procedure output 128*b* may indicate a success of individual ablation lesions as well as to provide the operator with an estimated likelihood of overall ablation success (based on patient history and imaging data, locations of the heart ablated, and success of the ablations performed in the context of data from patients who have undergone comparable procedures in the past). The during-procedure output 128*b* may correctly identify intracardiac electrograms in the areas of the heart targeted for ablation. During ablation, apparatus 100 for clinical decision support may highlight loss of electrograms in the areas being ablated (through mapping system/recording system and/or dedicated user interface 120). Processor 104 may user machine learning to assess and predict the success of cardiac ablation procedures involving a sophisticated integration and analysis of diverse data types. For example, processor 104 may consolidate patient history, which may include past cardiac conditions and outcomes of previous interventions, with high-resolution imaging data from modalities such as MRI, CT, or intracardiac echocardiography. This may be further enriched with real-time procedural data, such as the specific locations targeted for ablation and corresponding intracardiac electrograms, providing a comprehensive dataset for analysis. A machine learning model may be trained on extensive datasets, adept to recognizing patterns that indicate successful ablation, such as the diminishment or elimination of abnormal electrical signals which suggest effective interruption of arrhythmic pathways. To predict the overall success of the ablation, the machine learning model may employ a comparative analysis by matching current ablation data against historical data from similar procedures. Using predictive models like logistic regression or decision trees, processor 104 may estimate the likelihood of achieving a successful outcome based on the analysis of current and past procedural data. This predictive insight, along with real-time data and historical comparisons, may be presented to the clinician through a user interface 120. This interface may integrate with existing mapping or recording systems, offering dynamic updates and guidance that help optimize procedural strategies and improve patient outcomes. Apparatus 100 for clinical decision support may also provide the operator with a display indicating success of the ablation. At the end of the ablation procedure, apparatus 100 may also provide the operator with an estimate of ablation success (and durability) based on information obtained during each ablation of lesions, summary information (such as, contiguity of ablation lesions, intracardiac electro grams in ablated structures, other utilized metrics of ablation (e.g., power delivery, impedance, contact force, catheter stability, temperature, and the like)), results of objective measurements of ablation success (e.g., bidirectional pacing), and comparison of surface ECG before and after the ablation procedure.

Still referring to FIG. 1, a "post-procedure output," as used herein, is data generated regarding information applicable post to the performance of a procedure The post-procedure output 128*c* may be further divided into two stages, i.e., post-procedure evaluation of ablation (such as evaluation of ablation after some time or a predefined number of days) and assisting clinicians in advising patients. For example, the post-procedure output in the evaluation of ablation stage may include integrative assessment (utilizing each of the post-procedure input data) to assess lesion quality and contiguity, and post-ablation summative assessment of durability of ablation that would give the operator an estimate of a likelihood of AF recurrence based on chosen ablation strategy and quality of lesion delivery. In generating the integrative assessment, processor 104 may implement machine learning algorithms and statistical models configured to analyze this integrated dataset to evaluate the quality and contiguity of the ablation lesions. These analyses may help in assessing how well the lesions are formed, whether they are continuous and complete, and their alignment with the targeted arrhythmic pathways. The durability of the ablation may be assessed by examining the stability of the lesions over time through follow-up imaging and symptom evaluation. Predictive models may utilize this data to estimate the likelihood of atrial fibrillation (AF) recurrence as the model may consider the initial quality of the lesion delivery, patient-specific factors, and post-procedure recovery data to predict outcomes like two-year AF-free survival rates. In an embodiment, a predictive model may be trained on data including patient demographics and medical history, where factors like age, gender, and underlying health conditions are correlated with the outcomes of AF treatments. Additionally, detailed information about the ablation procedure itself, such as the type (radiofrequency or cryoablation), the number and location of lesions, and immediate post-procedure results, may provide correlations between specific treatment approaches and their long-term effectiveness.

Still referring to FIG. 1, the post-procedure output 128c for assisting the clinicians or operator for advising patients may include recommendations relating to, for example, oral anticoagulation therapy, frequency of clinic visits and ambulatory arrhythmia monitoring, and rate or rhythm control medication strategy. Generating such recommendations may include a processor 104 receiving a collection of detailed procedural data, patient-specific medical history, and immediate outcomes from the ablation, such as the quality and extent of lesions created. Additional inputs may include follow-up data from subsequent clinical evaluations and continuous monitoring, which help assess the patient's response to the ablation over time. These data elements provide a foundation for understanding the individual's specific health trajectory post-ablation. Processor 104 may use machine learning algorithms to assess the long-term effectiveness of the ablation, potential complications, and the overall stability of cardiac health post-procedure. By evaluating patterns and outcomes from similar previous cases, the algorithms may predict the need for ongoing treatments or interventions. For example, a machine learning model may be configured to analyze factors such as the completeness of pulmonary vein isolation and the patient's history of stroke or bleeding to recommend personalized oral anticoagulation therapy regimens. The training data may include data correlating user data 108 to post-procedure clinical and outcome data. Post-procedure clinical and outcome data may include collection of information gathered after a medical procedure, such as cardiac ablation, to evaluate its immediate and long-term effects. Post-procedure clinical and outcome data may include patient feedback regarding their health status, symptoms, and overall quality of life post-procedure. Based on this comprehensive analysis, the machine learning model may generate and output specific recommendations for post-ablation care. These may include the optimal oral anticoagulation therapy tailored to the patient's risk profile, suggested frequency for clinic visits to monitor recovery and detect any recurrence of arrhythmias, and strategies for rate or rhythm control if necessary. This output may be presented through a user interface 120, allowing clinicians to easily access and understand the advice, which they can then communicate to the patient.

Still referring to FIG. 1, the post-procedure output 128c may be provided in a user interface 120 relating to a mapping system, a recording system interface, or a dedicated user interface 120 with possible population of data in the EHR system. The post-procedure output 128c may provide input to clinicians regarding medical therapy (e.g., anticoagulation) and frequency of ambulatory arrhythmia assessments. The post-procedure output 128c may indicate an ablation success (e.g., two-year AF-free survival). This estimate could be used by clinicians to guide decision making regarding post-ablation management, including, a need for anticoagulation therapy after immediate post-procedure recovery, and a frequency of post-ablation visits.

Still referring to FIG. 1, generating a procedural output 128 based on the received user data 108 includes implementing a plurality of deep neural networks (DNNs)132a-132a The DNNs, (depicted as DNN1 132a, DNN2 132b and DNN 132c) are configured to receive the various types of input data as categorized by processor 104. For example, input data may include time series data 112 of user data 108, registered images of user data 108, and data extracted using language processing methods as described above. For example, the DNN1 132a may be configured to obtain or receive time series data 112. Further, based on the processing of the obtained time series data 112, the DNN1 132a is configured to generate a first set of feature vectors. In an example, the time series data 112 may include 12-lead ECG, EGM, echocardiography data, and the like. Processor 104 may train DNN1 132a with historical datasets containing labeled time series records from these devices. Each piece of data may be tagged with relevant outcomes, such as diagnoses, treatment results, or other clinical annotations that reflect the patient's cardiac status. This correlation allows the model to learn the relationships between the time series data and the clinical outcomes, enhancing its predictive accuracy in real-world scenarios.

Still referring to FIG. 1, subsequently, the DNN1 132a is trained to process time-series input data 204a to generate the corresponding first set of feature vectors. Continuing further, the DNN2 132b is configured to obtain or receive imaging data 116. Further, based on the processing of the imaging data, the DNN2 132b is configured to generate a second set of feature vectors. In an example, the imaging data may include CT data, MRI data, non-cardiac imaging data, and the like. Processor 104 may train DNN2 132 on a vast array of medical images, each labeled with information about the observed anatomical structures, pathologies, and potentially the outcomes of previous treatments. Such data helps the model learn to accurately interpret and analyze new imaging data. This labeling process establishes a direct correlation between the imaging data and the specific medical annotations, enabling the model to learn how various visual features are associated with different clinical conditions and outcomes. Moreover, the DNN3 132c may be configured to obtain or receive natural language data 136 of NPL model 124. In an example, the natural language data 136 may include historical data of the patient, such as previous prescriptions, communications with clinician or operator, and the like Based on the natural language data 136, the DNN3 132c may be configured to generate a third set of feature vectors. Processor 104 may train DNN3 132c on a corpus including clinical documents, medical records, and communication logs is required. Each document within this corpus must be annotated with details that highlight content relevance, sentiment, and specific medical insights. These annotations serve as the link between the text data and the interpretive labels, enabling the model to discern and learn the crucial relationships between the textual content and its clinical significance/outcome.

Still referring to FIG. 1, fused feature vector 140 is generated based on the first set of feature vectors, the second set of feature vectors, and the third set of feature vectors. A "fused feature vector," as used herein, is a single vector that combines multiple sets of features (or attributes) from different vectors or datasets into one comprehensive feature set. In an example, the fused feature vector 140 may represent features that may be used by the DNNs 132a-c in multi-dimensional numerical values. This technique may be used to enhance the performance of machine learning models by incorporating diverse information that can more accurately represent the complexity of the problem being analyzed. In generating fused feature vector 140, each feature vector may be normalized to ensure that no single feature dominates due to scale differences. This may involve scaling the features to a common range, such as 0 to 1, or transforming them to have a mean of zero and a variance of one. From each vector set, features that are most relevant to the task may be selected. This step helps reduce the dimensionality and avoids the curse of dimensionality, which can degrade the performance of machine learning models when too many irrelevant features are present. Processor 104 may implement methods such as Principal Component Analysis (PCA) or Autoencoders to reduce the number of features while retaining the most critical information from the data. Fusion may include concatenating the normalized and possibly reduced feature vectors end-to-end. This concatenated vector may form the fused feature vector, which retains information from all original vectors. In another embodiment, fusion may include using a neural network or another machine learning model to learn an optimal combination of features. This could mean a weighted sum where weights are learned based on how informative each feature is regarding the prediction task.

Stil referring to FIG. 1, in generating a pre-procedure output 128a and the post-procedure output 128c, processor 104 may train a fused classifier 144 based on the fused feature vector 140. A "fused classifier," as used herein, is a machine learning, also known as an ensemble classifier, which combines the predictions of multiple classifiers/models to improve the overall accuracy and robustness of predictions. The fused classifier may include machine learning models, algorithms and training data as described above, in addition to the fused feature vector 140 in generating the outputs. In an example, the fused classifier 144 may be configured to combine multiple classification decisions relating to the input data at different stages or points of patient care and generate better classification results than any single classifier.

Still referring to FIG. 1, in generating a during-procedure output 128b, processor 104 may train a fused object detection model 148 configured to generate the during-procedure output 128b based on the fused feature vector 140. A "fused object detection model," as used herein a machine learning model trained to detect a presence or an absence of specific objects such as images and videos. In one example, the fused object detection model 148 may be configured to detect a presence or an absence of PVP or PVI and PWI signal. Fused object detection may work in conjunction with the plurality of machine learning models and algorithms as disclosed above to collectively output the during-procedure output 128b.

Still referring to FIG. 1, according to several exemplary embodiments, hypothetical vignettes describing four distinct scenarios that may be encountered by an operator at the time of an ablation for atrial fibrillation/flutter are provided. Ablation procedures for persistent atrial fibrillation and atypical atrial flutter are generally associated with higher rates of post-procedure arrhythmia recurrence than ablations for paroxysmal atrial fibrillation. In an example, a patient may have paroxysmal atrial fibrillation with no prior ablation procedures. For example, a 38-year-old woman may experience intermittent, self-terminating atrial fibrillation with no prior history of ablations and no history of structural abnormalities of the heart. In this case, the operator may perform ablations in areas of the pulmonary veins. In particular, electrical isolation of the veins is checked. Further, during post-ablation arrhythmia monitoring, no recurrence of AF is detected for 6 months after the procedure. Because the CHADS-VASC score is 1 for this patient and she is no longer experiencing AF, the patient asks the physician if it is possible to discontinue oral anticoagulants after 6 months of the procedure. In the present example, when apparatus 100 is deployed for clinical decision support, during the procedure, i.e., during-procedure stage, apparatus 100 may provide an assessment of a likelihood of AF recurrence, based on the historical data, imaging data, surface ECG at baseline, as well as observations of changes in intracardiac electrograms and surface ECG during ablation. To this end, the calculated likelihood of recurrence may help the operator to take an informed decision regarding holding or continuing the oral anticoagulant after the procedure.

Still referring to FIG. 1, in another example, a patient may have persistent atrial fibrillation with no prior ablation procedures. For example, a 62-year-old man may have hypertension and a high burden of persistent atrial fibrillation. Herein, the deployment of apparatus 100 for clinical decision support before the procedure may guide the operator or the clinician regarding where ablation lesions should be placed (e.g., pulmonary veins or ablation of the posterior wall). In addition, apparatus 100 may be utilized in the during-procedure stage for clinical decision support relating to information regarding likelihood of recurrence, and post-procedure stage for post-procedure management. In yet another example, a patient may have persistent atrial fibrillation and may be undergoing a redo ablation procedure or a second ablation procedure. For example, a 62-year-old man may have hypertension and a high burden of persistent atrial fibrillation. Herein, the deployment of apparatus 100 for clinical decision support before the procedure may guide the clinician regarding where ablation lesions should be placed based on the patient's individual history, anatomic data, and ECGs. In this regard, different ablation strategies could be utilized (e.g., pulmonary veins ablation and/or posterior wall ablation). Further, apparatus 100 may be deployed for the clinical decision support during the procedure to provide the operator with information regarding where ablation lesions were delivered previously and where it should be delivered now. For example, the information regarding prior ablation could also be utilized to guide ablation delivery. Apparatus 100 may also provide the operator with information regarding likelihood of arrhythmia recurrence, which can influence post-procedure management. In yet another example, a patient may have persistent atrial fibrillation and atrial flutter. For example, a 62-year-old man may have hypertension and a high burden of persistent atrial fibrillation. Herein, the deployment of apparatus 100 for clinical decision support before the procedure to guide the clinician regarding where ablation lesions should be placed for AF (e.g., pulmonary veins, posterior wall, and/or specific sites to target atrial flutter including the mitral isthmus). Apparatus 100 may be deployed for the clinical decision support in the pre-procedure stage to identify the location of the atrial flutter. Further, apparatus 100 may be deployed for the clinical decision support during the procedure to provide the operator with information regarding likelihood of recurrence, which can influence post-procedure management.

Still referring to FIG. 1, to this end, apparatus 100 for clinical decision support software would be used for all phases of patient care. Input information and user interface 120 would be adjusted depending on a stage or point of care (such as pre-ablation procedure, post-ablation procedure, or during ablation procedure). In particular, during the pre-ablation procedure stage, apparatus 100 provides the ability to integrate multiple types of data before the procedure to inform or devise ablation approach. Moreover, during the during-ablation procedure stage, apparatus 100 provides the ability to integrate multiple types of data (including dynamic changes in surface ECG and intracardiac electrograms associated with ablation, as well as dynamic changes in other ablation metrics) to assess likelihood of ablation success. Further, during the post-ablation procedure stage, apparatus 100 provides the ability to integrate multiple types of data to inform clinicians regarding medical therapy (e.g., anticoagulation) and frequency of ambulatory arrhythmia assessments.

Still referring to FIG. 1, to this end apparatus 100 of the present disclosure provides an ML-based clinical decision support tool that can help operators, such as physicians, clinicians, and the like to identify the appropriate regions of the heart to ablate and to assess when effective ablations have been delivered. Multiple data types, such as intracardiac electrogram, surface ECG, imaging data, patient history, and the like are incorporated by apparatus 100. Further, apparatus 100 for clinical decision support is accessible at several points in the patient journey, such as pre-ablation procedure stage or procedural planning stage, during the ablation procedure, and post-ablation procedure stage or post-ablation management. As a result, apparatus 100 provides an ML-based clinical decision support tool for identification of intracardiac electrograms during ablation procedures. This may help inexperienced operators and low-volume operators, but could be used by experienced operators to reduce procedure time and improve results. For example, the Pulmonary vein potential (PVP) identification during ablation in the context of sinus rhythm or atrial pacing may be performed by apparatus 100 employing object detection model for effective ablation delivery plan and post-procedure management. For example, apparatus 100 may help an operator in understanding if their catheter is in an appropriate location for ablation, in the pre-procedure stage. Moreover, apparatus 100 may help an operator in understanding if the ablation procedure was effective, success rate, and chances of AR recurrence, in the during-procedure stage. In addition, apparatus 100 may help in quick detection of abnormal electrical activity, thereby improving procedural efficiency. Subsequently, apparatus 100 ensures reduced risk of human error which can cause over- or under-ablation, reduced complication risk, better post-procedure success confirmation, and ability to classify/detect other signals of interest during procedure.

Figure 2A:
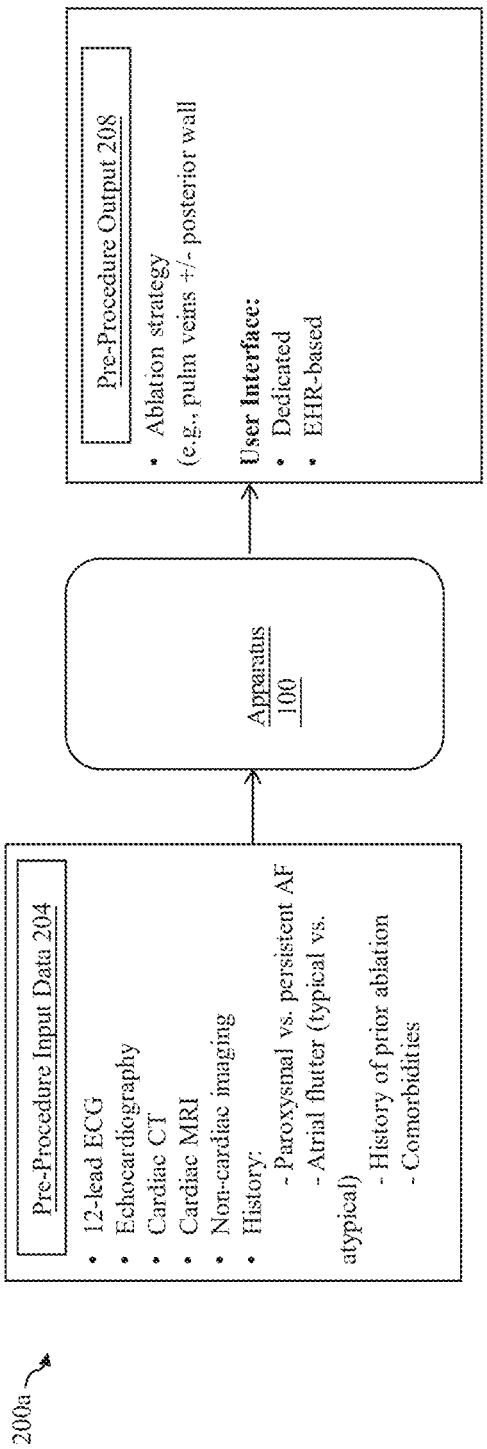
FIGS. 2A-2C are schematic embodiments of procedural outputs.
Figure 2B:
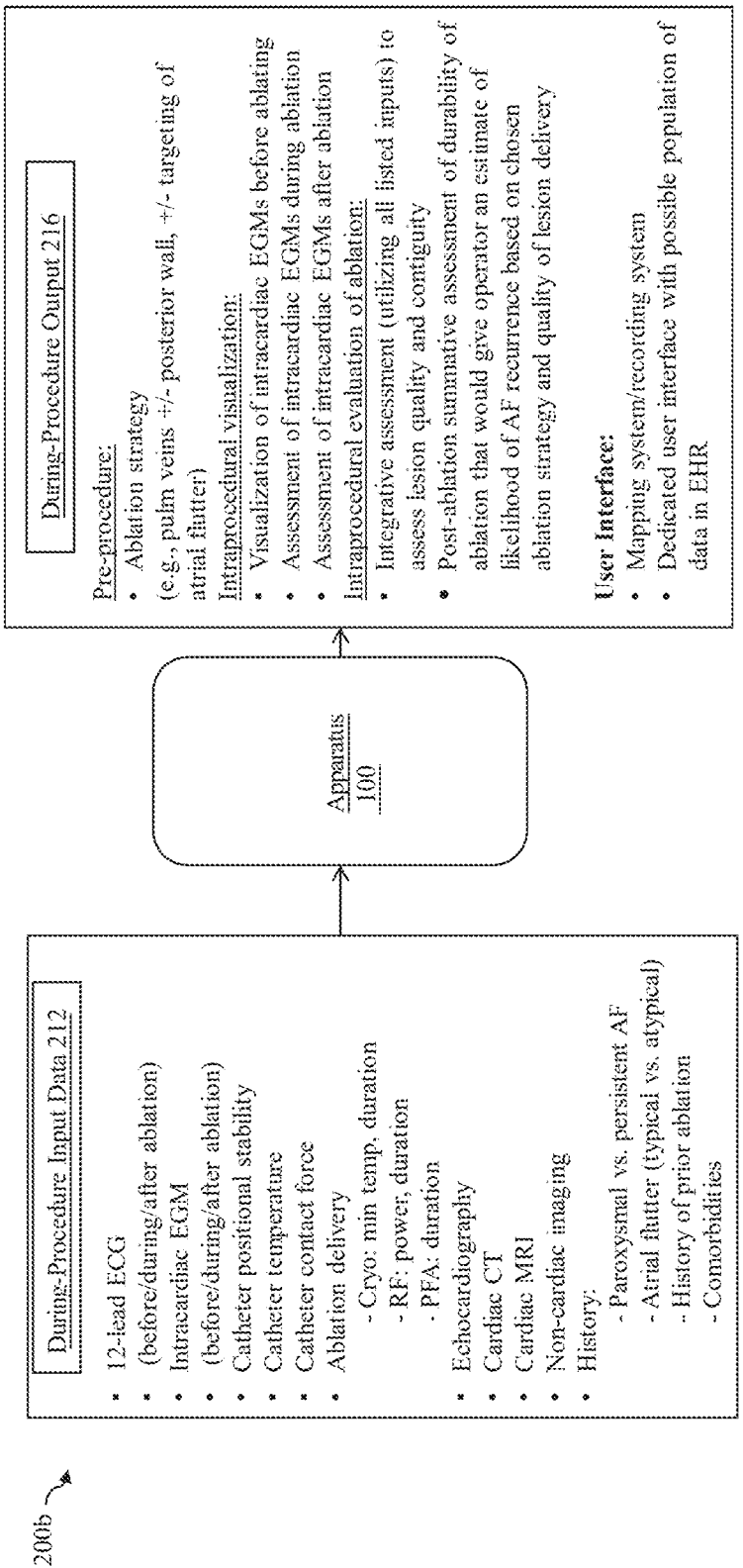
Figure 2C:
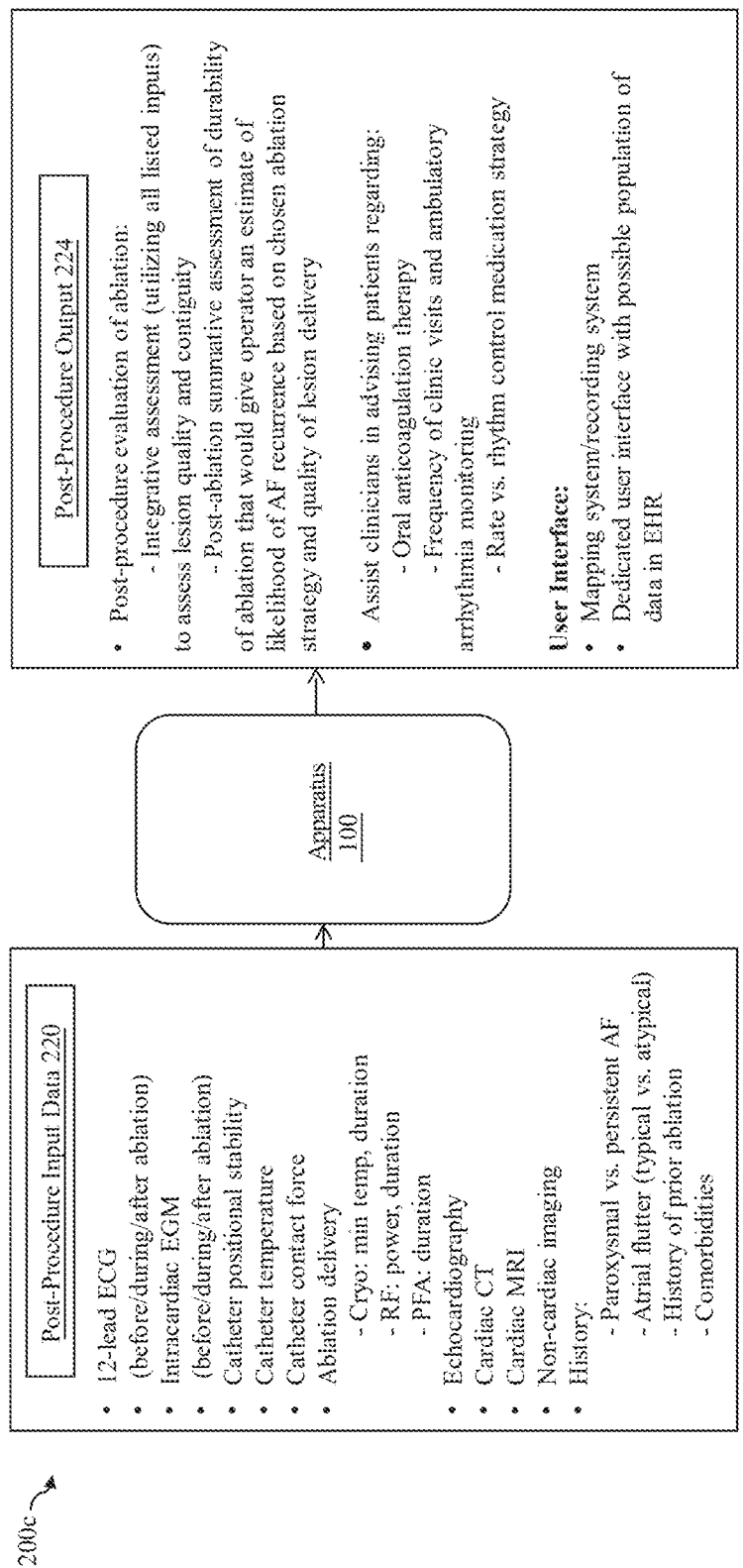

Referring now to FIGS. 2A-2C, schematic embodiments of procedural outputs are illustrated. FIG. 2A illustrates a schematic 200a for implementation of apparatus 100 for generating a pre-procedure output 208, in accordance with an example embodiment. As shown by FIG. 2A, apparatus 100 is configured to receive pre-procedure input data 204. The pre-procedure input data 204 may include, but is not limited to, 12-lead ECG data, echocardiography data, Cardiac computed tomography (CT) data, cardiac magnetic resonance imaging (MRI) data, non-cardiac imaging data, and historical data (for example, paroxysmal and persistent AF data, typical and/or atypical atrial flutter data, and history of prior ablation, and comorbidities data). FIG. 2B illustrates a schematic 200b for implementation of apparatus 100 for generating a during-procedure output 216, in accordance with an example embodiment. As shown by FIG. 2B, apparatus 100 may be configured to receive during procedure input data 212. The during procedure input data 212 may include, but is not limited to, the 12-lead ECG data (before/during/after ablation), local intracardiac electrogram (EGM) data (before/during/after ablation), catheter tip positional stability data, catheter tip temperature data, catheter contact force data, power delivery data, contact force, ablation delivery data (such as, minimum temp and duration for Cryoablation procedure; power and duration for RF-based ablation procedure; and duration for PFA-based ablation procedure), contiguity of ablation lesions, echocardiography data, intracardiac electrograms in ablated structures, other utilized metrics of ablation (such as power delivery, impedance, contact force, catheter stability, temperature), results of objective measures of ablation success, cardiac CT data, comparison of surface ECG before and after the procedure cardiac MRI data, non-cardiac imaging data, and history data of the patient (such as, paroxysmal AF or persistent AF related data, typical or atypical atrial flutter data, prior ablation historical data, and comorbidities data). FIG. 2C illustrates a schematic 200c for implementation of apparatus 100 for generating a post-procedure output post-procedure input data 224, in accordance with an example embodiment. As shown by FIG. 2C, apparatus 100 is configured to receive post-procedure input data 220. The post-procedure input data 220 may include, but is not limited to, 12-lead ECG data (before/during/after ablation), echocardiography data, Cardiac CT data, cardiac MRI data, non-cardiac imaging data, historical data (such as, paroxysmal or persistent AF data, typical or atypical atrial flutter data, historical prior ablation data, and comorbidities data).

Figure 3:
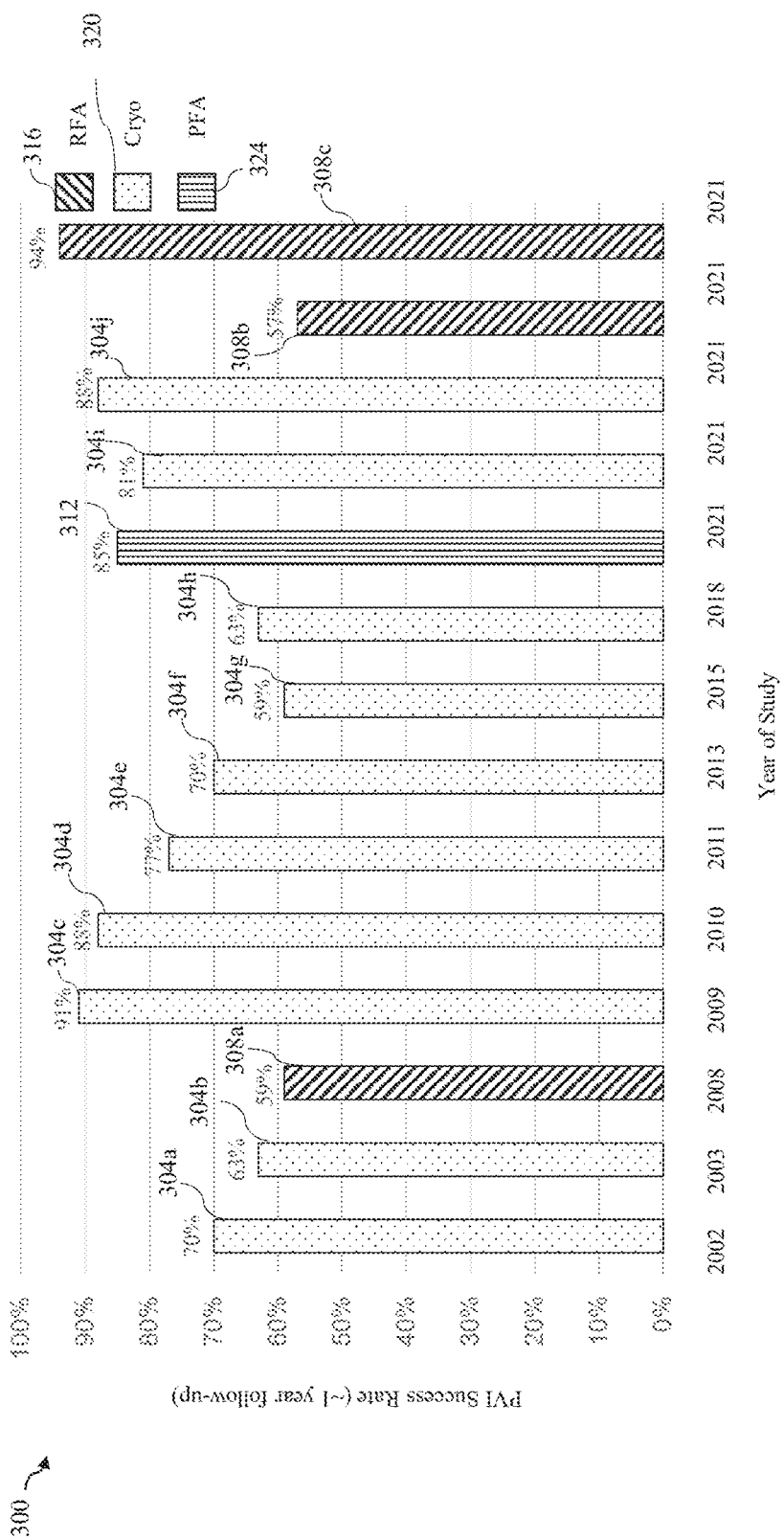
FIG. 3 is a graph illustrating a variability in pulmonary vein isolation (PVI) success rate.

Referring to FIG. 3, there is shown a graph 300 illustrating a variability in pulmonary vein isolation (PVI) success rate, in accordance with an example embodiment. The graph 300 indicate success rates 304a, 304b, 304c, 304d, 304e, 304f, 304g, 304h, 304i, and 304j in corresponding years, 2002, 2003, 2009, 2010, 2011, 2013, 2015, 2018, 2021 and 2021, respectively. For example, these different success rates 304a, 304b, 304c, 304d, 304e, 304f, 304g, 304h, 304i, and 304j in the corresponding years are determined based on, for example, Circ 2002; 105:1077-1081, Circ 2003; 107:3176-3183, Circ EP 2009; 2:113-119, Eur Heart J 2010; 31:1344-1356, JCE 2011; 22:973-981, STOPAF, JACC 2013; 61:1713-1723, STARAFII, NEJM 2015; 372: 18121822, CASTLE AF, NEJM 2018; 378:417-427, Heart Rhythm 2021; S15475271(21)02347-X, and CHARISMA, JCE 2021; 32:1540-1548, respectively. To this end, the success rates 304a, 304b, 304c, 304d, 304e, 304f, 304g, 304h, 304i, and 304j in corresponding years correspond to success of a cryoablation (cryo) procedure 320. Further, the graph 300 indicates success rates 308a, 308b, and 308c in corresponding years, 2008, 2021 and 2021 that are determined based on, for example, Europace 2008; 10:1271-1276, EARLY-AF, NEJ 2021; 384:305-315, and JCE 2021; 32:2933-2942. For example, the success rates 308a, 308b, and 308c in the corresponding years correspond to success of a radiofrequency ablation (RFA) procedure 316. Similarly, the graph 300 indicates a success rate 312 in the year 2021 based on JACC EP 2021; 7:614-627 corresponding to a success of a pulse filed ablation (PFA) procedure 324.

Figure 4:
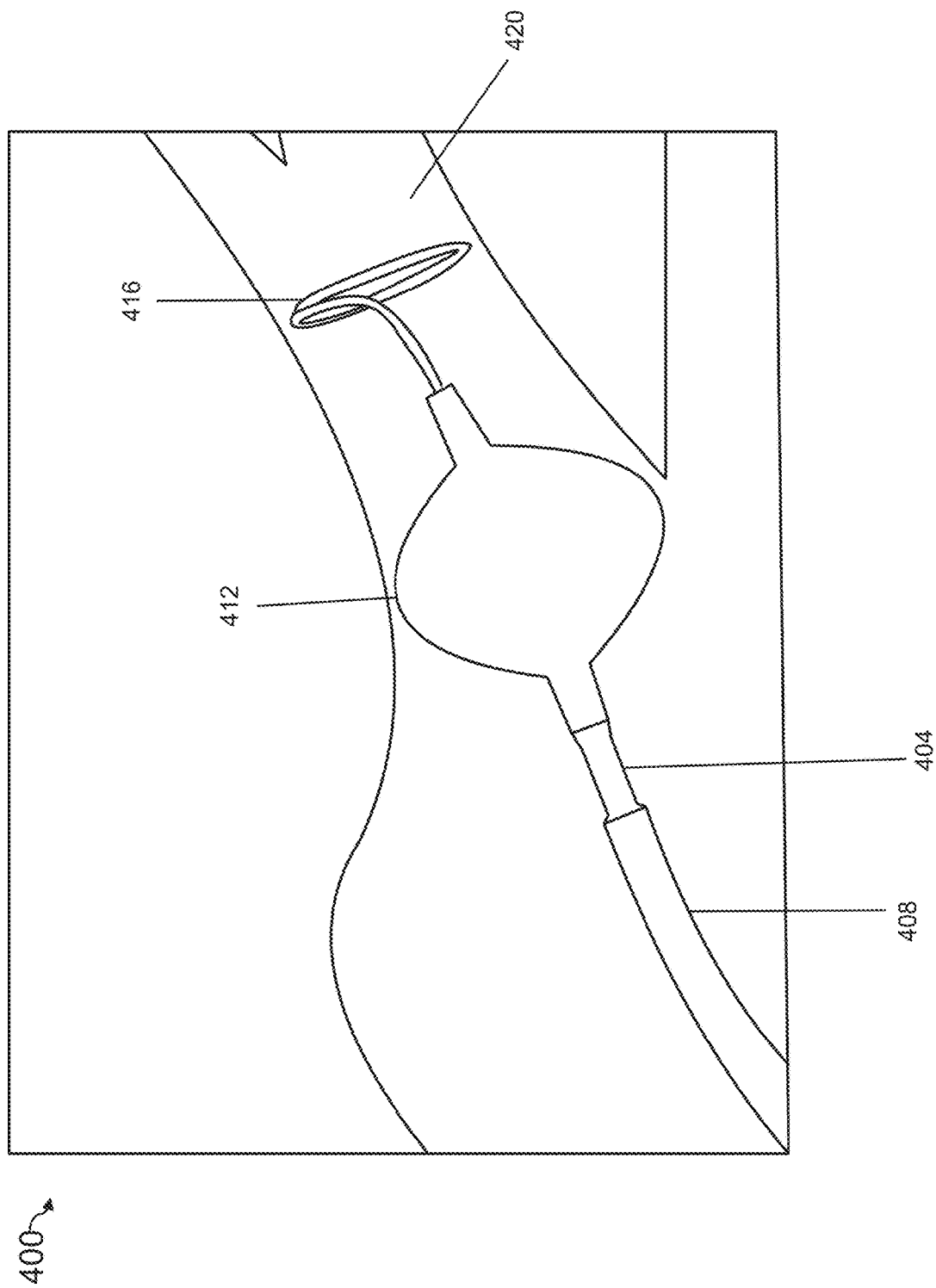
FIG. 4 is a schematic for implementation of a cryoablation procedure.

Referring now to FIG. 4 a schematic for implementation of a cryoablation procedure 400, in accordance with an example embodiment is illustrated. According to present example, the cryoablation procedure 400 includes insertion of a cryo-ballon catheter 404 in a pulmonary vein 420. The cryo-ballon catheter 404 is attached to a 12-French steerable sheath 408 at rear end and to an integrated circular mapping catheter 416 and cryo-ballon 412 at frond end. it may be noted that cryoablation procedure 400 is only exemplary, and in other embodiments, RF-based or PFA-based ablation procedures may be performed. In an example, apparatus 100 is used to generate consistent ablation protocol, perform consistent data collection and EGM measurement (such as, before, during, and after ablation), and enable first-time ablation (such as, for paroxysmal AF, sinus rhythm or atrial pacing).

Figure 5:
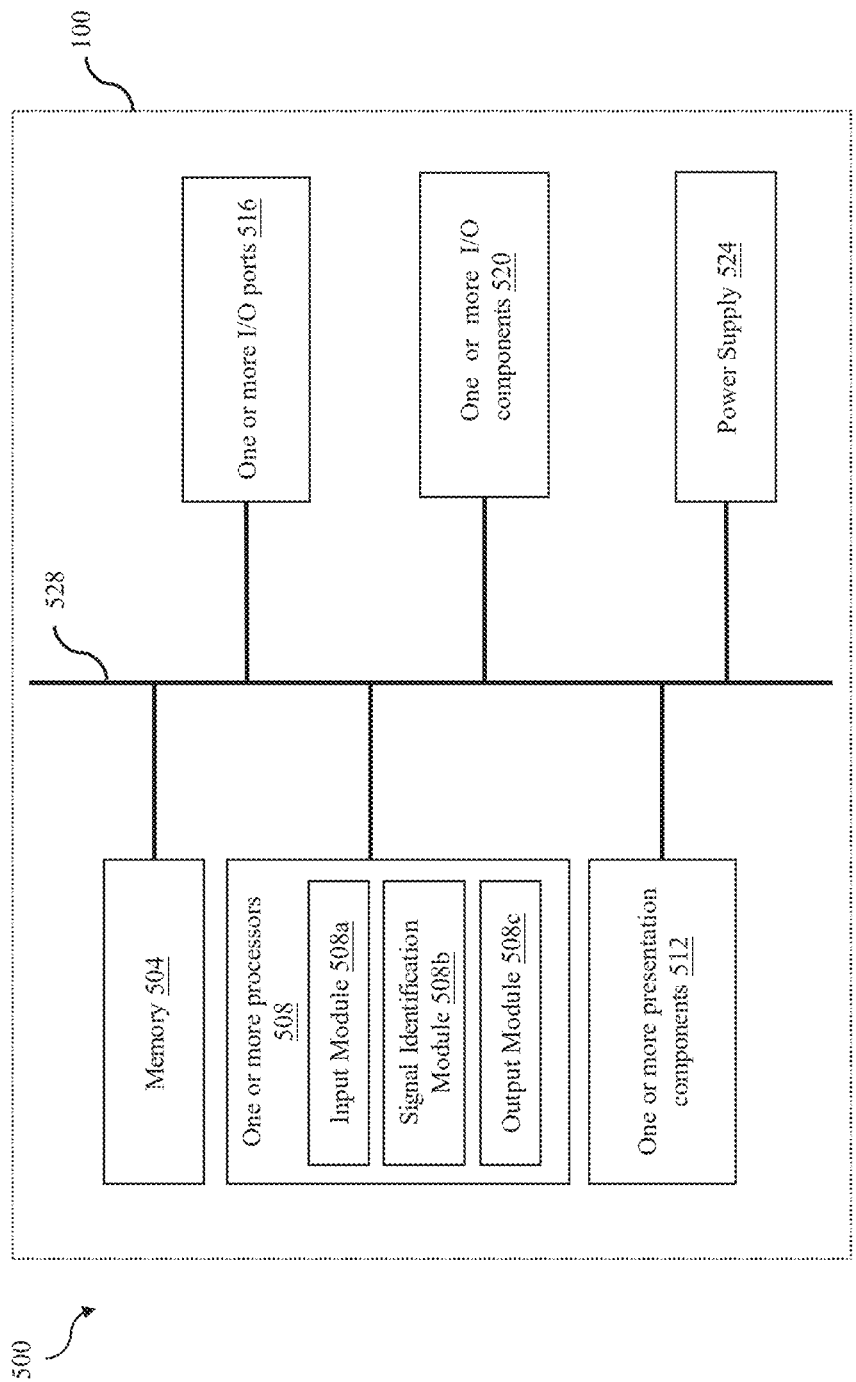
FIG. 5 a block diagram of an apparatus for generating clinical decision support.

Referring now to FIG. 5, a block diagram 500 of apparatus 100 of FIGS. 2A-2C which is used for generating a clinical decision support output, in accordance with an example embodiment of the disclosure is illustrated. The internal components of apparatus 100 includes a bus 528 that directly or indirectly couples the following devices: a memory 504, one or more processors 508, one or more presentation components 512, one or more input/output (I/O) ports 516, one or more input/output components 520, and an illustrative power supply 524. The one or more processors 508 may further include modules, such as an input module 508a configured to retrieve or receive multiple types of patient data, for example, surface electrocardiogram (ECG), intracardiac electrocardiogram (ECG), cardiac imaging, and patient historical data. The modules may further include a signal identification module 508b (also referred to as signal identification tool) that includes a set of machine learning-based models. The signal identification module may be deployed at multiple points during a patient's care journey, such as before ablation procedure, during ablation procedure, or after ablation procedure, to provide clinical decision support based on the processing of the multiple types of patient data. The modules may further include an output module 508c that provides a user interface to enable users, such as health care providers, operators, clinicians, and the like to access the system for clinical decision support. The bus 528 represents what may be one or more buses (such as an address bus, data bus, or combination thereof). Although the various blocks of FIG. 5 are shown with lines for the sake of clarity, in reality, delineating various components is not so clear, and metaphorically, the lines would more accurately be grey and fuzzy. For example, one may consider a presentation component such as a display device to be an I/O component. It may be understood that the diagram of FIG. 5 is merely illustrative of apparatus 100 that can be used in connection with one or more embodiments of the present invention. The distinction is not made between such categories as "user device", "server", "computing device", "laptop," "hand-held device," "mobile phone," "tablet," and the like, as all are contemplated within the scope of FIG. 5.

Still referring to FIG. 5, the memory 504 includes, but is not limited to, non-transitory computer readable media that stores program code and/or data for longer periods of time such as secondary or persistent long term storage, like RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information. Apparatus 100 includes one or more processors 508 that read data from various entities such as the memory 504 or I/O components 520. The one or more presentation components 512 present data indications to the system or a user device. Exemplary presentation components include a display device, speaker, printing component, vibrating component, and the like The one or more I/O ports 516 allow apparatus 100 to be logically coupled to other devices including the one or more I/O components 520, some of which may be built in. Illustrative components include a microphone, joystick, game pad, satellite dish, scanner, printer, wireless device, and the like.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of.

Figure 6:
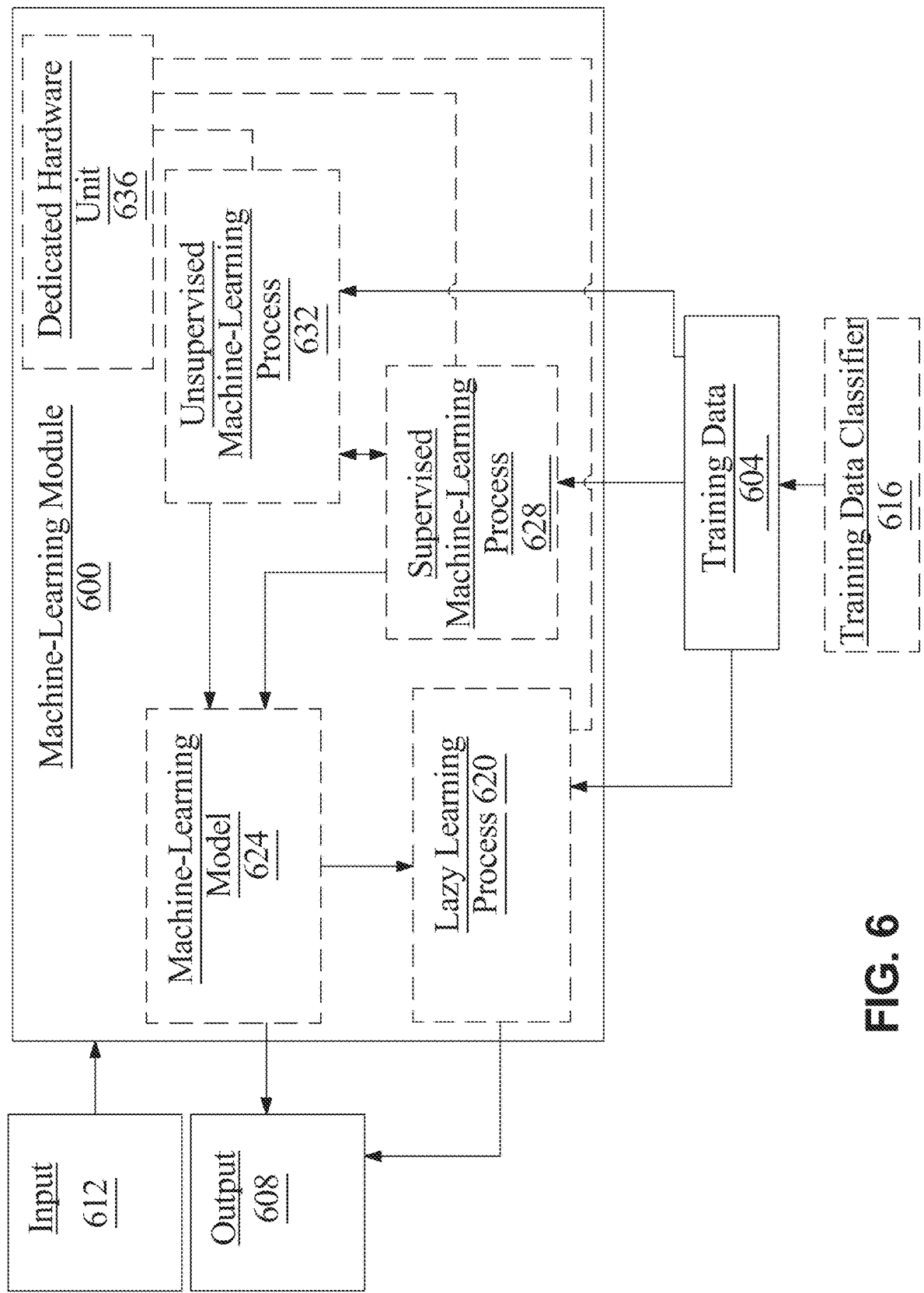
FIG. 6 is an exemplary embodiment of a machine-learning module.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm instantiated in hardware or software logic, data structures, and/or functions that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to identify specific risk profiles, such as a cohort of persons with a predisposition for atrial fibrillation based on genetic factors and lifestyle choices, and/or other analyzed items and/or phenomena for which a subset of training data may be selected.

Still referring to FIG. 6, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 6, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 6, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 6, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 6, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 6, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 6, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 6, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 6, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 6, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 6, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25$^{th}$ percentile value and the 50$^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alterative or additional approaches that may be used for feature scaling.

Further referring to FIG. 6, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

With further reference to FIG. 6, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 6, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 632 may not require a response variable; unsupervised processes 632may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 6, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 6, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 6, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 6, one or more processes or algorithms described above may be performed by at least a dedicated hardware unit 636. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 636 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 636 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 636 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 7:
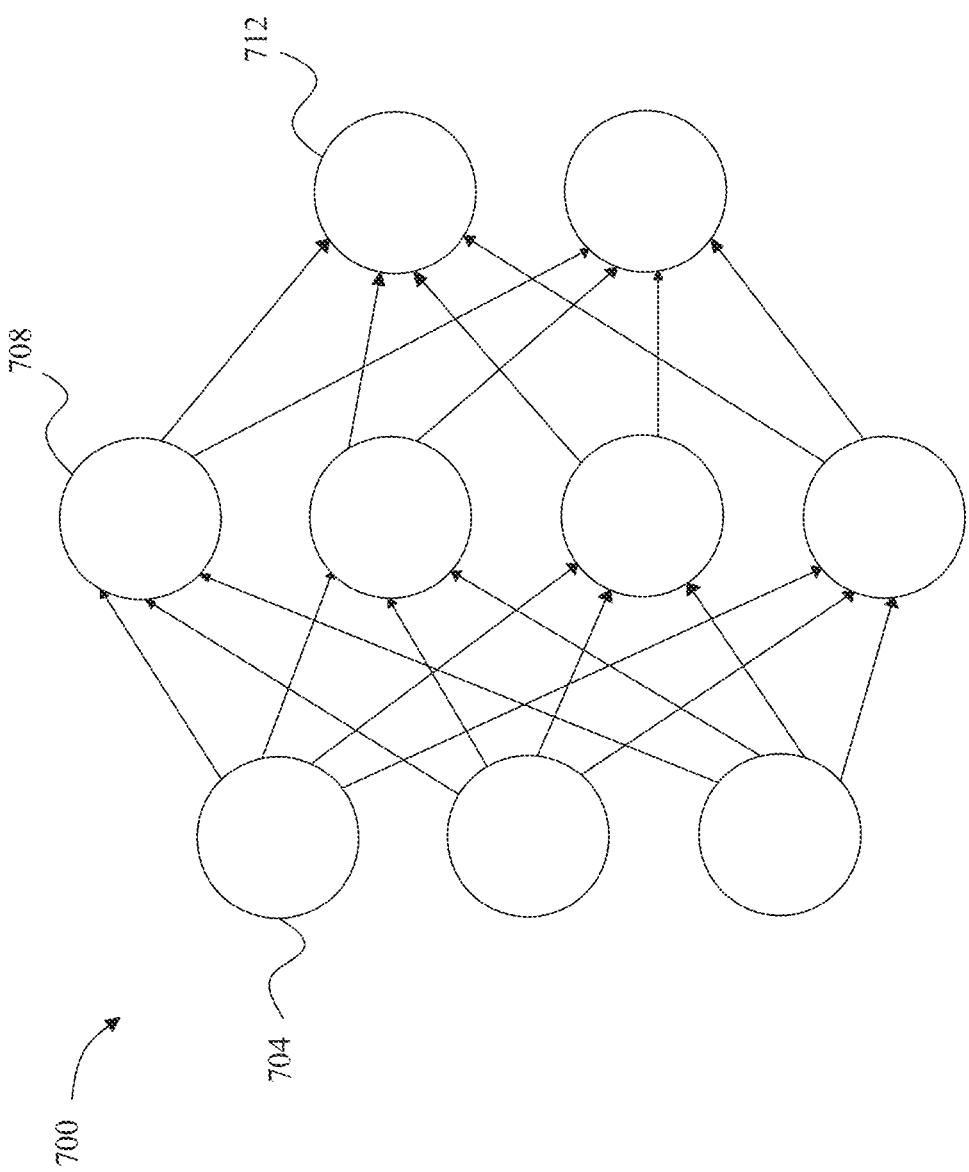
FIG. 7 is an exemplary embodiment of neural network.

Referring now to FIG. 7, an exemplary embodiment of neural network 700 is illustrated. A neural network 700 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 704, one or more intermediate layers 708, and an output layer of nodes 712. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further nonlimiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 8:
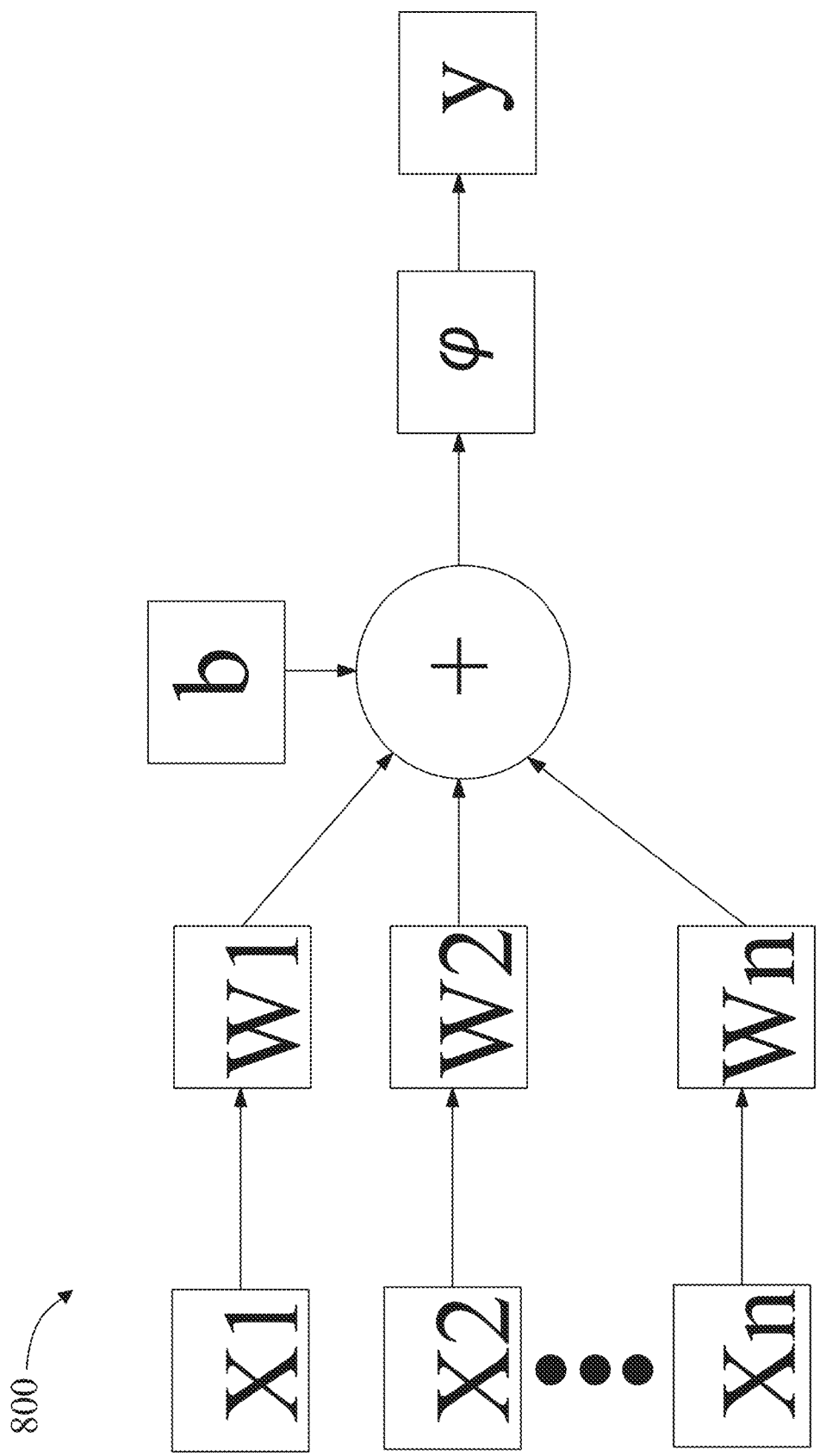
FIG. 8 is an exemplary embodiment of a node of a neural network.

Referring now to FIG. 8, an exemplary embodiment of a node 800 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as ƒ(x)=tanh²(x), a rectified linear unit function such as ƒ(x)=max(0, x), a "leaky" and/or "parametric" rectified linear unit function such as ƒ(x)=max (ax, x) for some a, an exponential linear units function such as $$f(x) = \begin{cases} x & \text{for } x \geq 0 \\ \alpha(e^x - 1) & \text{for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as ƒ(x)=x*sigmoid(x), a Gaussian error linear unit function such as ƒ(x)=a(1+tanh(√2/π(x+bx^r))) for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 9:
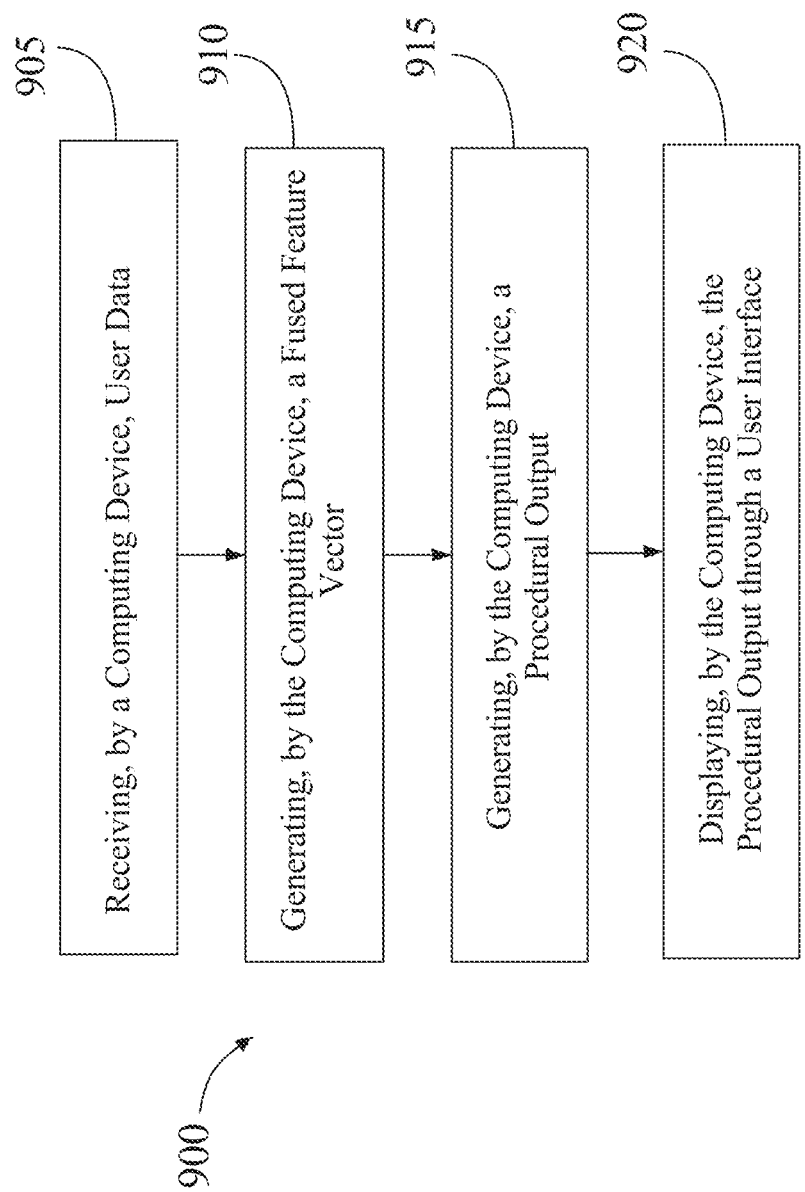
FIG. 9 is an exemplary flow chart of a method for generating clinical decision support.

Referring now to FIG. 9, an exemplary flow chart of a method 900 for generating clinical decision support. At step 905, method 900 includes receiving, by a computing device, user data. This may be implemented as disclosed in FIGS. 1-8. At step 910, method 900 includes generating, by the computing device, a fused feature vector correlating the user data to a plurality of clinical outcomes by training a plurality of deep neural networks (DNNs) to output a first set of feature vectors, a second set of feature vectors, a third set of feature vectors, and fusing the first, second, and third set of features vectors to form the fused feature vector. This may be implemented as disclosed in FIGS. 1-8. training the plurality of DNNs may include training a first DNN with time series data of the user data correlated to clinical outcomes to output the first set of feature vectors. Training the plurality of DNNs may include training a second DNN with image data of the user data correlated to clinical outcomes to output the second set of feature vectors. Training the plurality of DNNs may include training a third DNN with text data of user data correlated to clinical outcomes to output the third set of feature vectors. At step 915, method 900 includes generating, by the computing device, a procedural output using the feature vector. This may be implemented as disclosed in FIGS. 1-8. The procedural output may include a pre-procedure output, a during-procedure output, and a post-procedure output. The pre-procedure output may include an ablation strategy outlining focus on key aspects of cardiac ablation prior to an ablation procedure. The during-procedure output may include an integrative assessment data assessing lesion quality and contiguity implemented in an intraprocedural visualization stage of an ablation procedure. The post-procedure output may include a post-ablation summative assessment of durability of ablation estimating a likelihood of atrial fibrillation recurrence after an ablation procedure. Generating the procedural output may include training a fused feature classifier based on the fused feature to output a pre-procedure output and a post-procedure output. Generating the procedural output may include training a fused object detection model based on the fused feature vector to output a during-procedure output. At step 920, method 900 includes display, by the computing device, the procedural output through a user interface. This may be implemented as disclosed in FIGS. 1-8

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
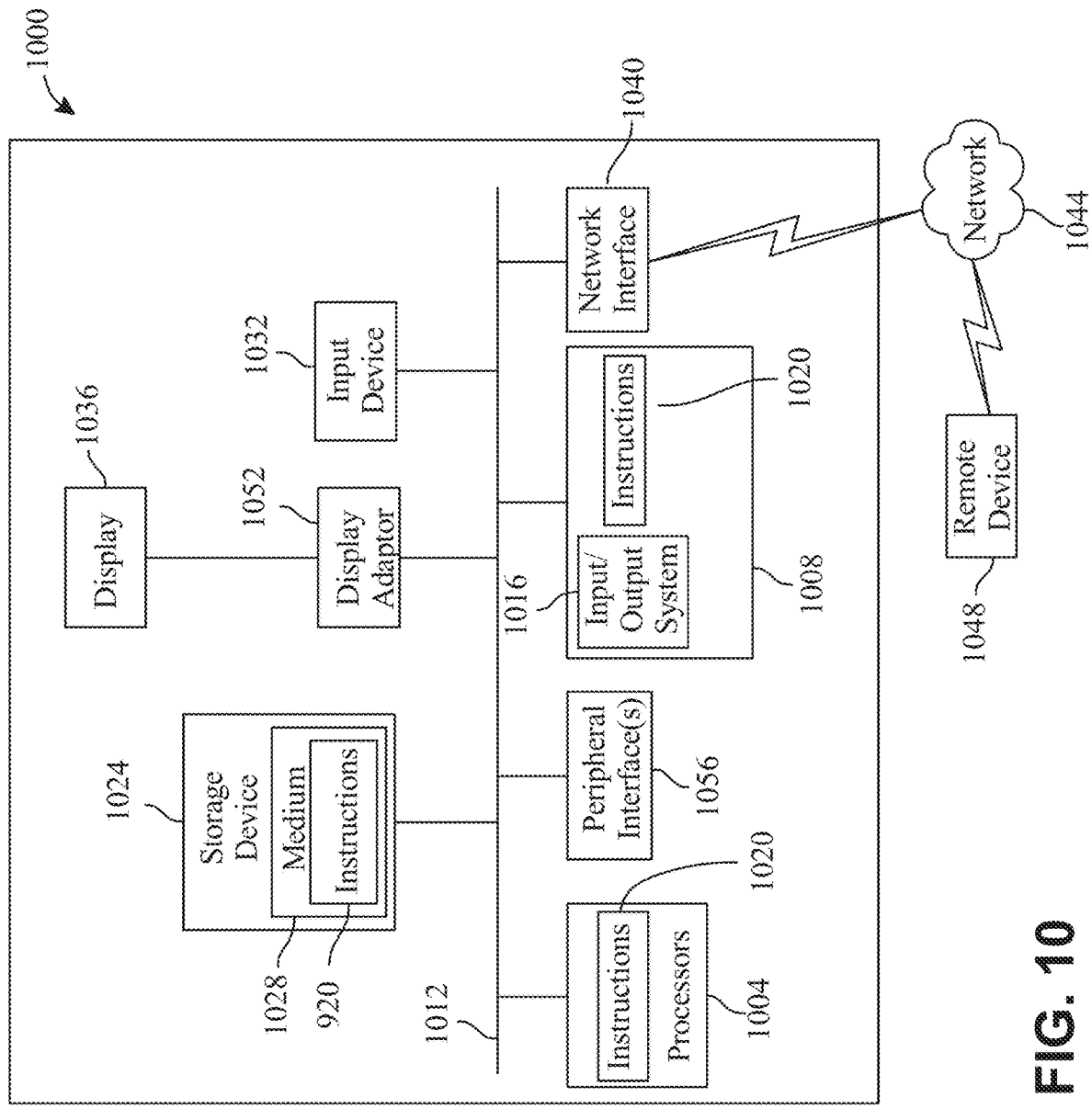
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, and the like) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, and the like) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generating clinical decision support, wherein
   the apparatus comprises:
   at least a processor;
   a computer-readable storage medium communicatively connected to the at least a processor, wherein the computer-readable storage medium contains instructions configuring the at least processor to:
   receive user data associated with a subject, the user data comprising:
      electrocardiogram (ECG) data comprising a plurality of signals representative of an electrical activity of a heart of the subject;
      image data comprising a plurality of images associated with the heart of the subject; and
      user historical data comprising a plurality of records;
   generating, using a first deep neural network (DNN), a first set of feature vectors representative of the ECG data;
   generating, using a second DNN, a second set of feature vectors representative of the image data;
   generating, using a third DNN, a third set of feature vectors representative of the user historical data; and
   generate a set of dimensionally reduced feature vectors for each of the first set, the second set, and the third set of feature vectors; fusing the first, second, and third set of dimensionally reduced features vectors to form the fused feature vector;
   generate a procedural output using the fused feature vector; and
   display the procedural output through a user interface.

2. The apparatus of claim 1, wherein the first DNN is trained with time series data of exemplary user data correlated to clinical outcomes to output the first set of feature vectors.

3. The apparatus of claim 1, wherein the second DNN is trained with image data of exemplary user data correlated to clinical outcomes to output the second set of feature vectors.

4. The apparatus of claim 1, wherein the third DNN is trained with natural language data of exemplary user data correlated to clinical outcomes to output the third set of feature vectors.

5. The apparatus of claim 1, wherein the procedural output comprises a pre-procedure output, a during-procedure output, and a post-procedure output.

6. The apparatus of claim 5, wherein the pre-procedure output comprises an ablation strategy outlining focus on key aspects of cardiac ablation prior to an ablation procedure.

7. The apparatus of claim 5, wherein the during-procedure output comprises an integrative assessment data assessing lesion quality and contiguity implemented in an intraprocedural visualization stage of an ablation procedure.

8. The apparatus of claim 5, wherein the post-procedure output comprises a post-ablation summative assessment of durability of ablation estimating a likelihood of atrial fibrillation recurrence after an ablation procedure.

9. The apparatus of claim 1, wherein generating the procedural output comprises training a fused feature classifier based on the fused feature vector to output a pre-procedure output and a post-procedure output.

10. The apparatus of claim 1, wherein generating the procedural output comprises training a fused object detection model based on the fused feature vector to output a during-procedure output.

11. A method for generating clinical decision support, wherein the method comprises:
    receiving, by a computing device, user data associated with a subject, the user data comprising:
        electrocardiogram (ECG) data comprising a plurality of signals representative of an electrical activity of a heart of the subject;
        image data comprising a plurality of images associated with the heart of the subject; and
        user historical data comprising a plurality of records;
    generating, using a first deep neural network (DNN), a first set of feature vectors representative of the ECG data;
    generating, using a second DNN, a second set of feature vectors representative of the image data;
    generating, using a third DNN, a third set of feature vectors representative of the user historical data; and
    generate a set of dimensionally reduced feature vectors for each of the first set, the second set, and the third set of feature vectors; fusing the first, second, and third set of dimensionally reduced features vectors to form the fused feature vector;
    generating, by the computing device, a procedural output using the fused feature vector; and
    displaying, by the computing device, the procedural output through a user interface.

12. The method of claim 11, wherein the first DNN is trained with time series data of exemplary user data correlated to clinical outcomes to output the first set of feature vectors.

13. The method of claim 11, wherein the second DNN is trained with image data of exemplary user data correlated to clinical outcomes to output the second set of feature vectors.

14. The method of claim 11, wherein the third DNN is trained with natural language data of exemplary user data correlated to clinical outcomes to output the third set of feature vectors.

15. The method of claim 11, wherein the procedural output comprises a pre-procedure output, a during-procedure output, and a post-procedure output.

16. The method of claim 15, wherein the pre-procedure output comprises an ablation strategy outlining focus on key aspects of cardiac ablation prior to an ablation procedure.

17. The method of claim 15, wherein the during-procedure output comprises an integrative assessment data assessing lesion quality and contiguity implemented in an intraprocedural visualization stage of an ablation procedure.

18. The method of claim 15, wherein the post-procedure output comprises a post-ablation summative assessment of durability of ablation estimating a likelihood of atrial fibrillation recurrence after an ablation procedure.

19. The method of claim 11, wherein generating the procedural output comprises training a fused feature classifier based on the fused feature vector to output a pre-procedure output and a post-procedure output.

20. The method of claim 11, wherein generating the procedural output comprises training a fused object detection model based on the fused feature vector to output a during-procedure output.

* * * * *